US009733243B2

(12) United States Patent
Tsuzaka

(10) Patent No.: US 9,733,243 B2
(45) Date of Patent: Aug. 15, 2017

(54) TEST METHOD FOR RHEUMATOID ARTHRITIS AND KIT FOR RHEUMATOID ARTHRITIS TEST

(75) Inventor: Kensei Tsuzaka, Chiba (JP)

(73) Assignee: KAYTEEBIO, CO. & LTD., Chiba (JP)

( * ) Notice: Subject to any disclaimer, the term of this patent is extended or adjusted under 35 U.S.C. 154(b) by 857 days.

(21) Appl. No.: 13/695,486

(22) PCT Filed: Jun. 14, 2011

(86) PCT No.: PCT/JP2011/063563
§ 371 (c)(1),
(2), (4) Date: Nov. 1, 2012

(87) PCT Pub. No.: WO2012/081271
PCT Pub. Date: Jun. 21, 2012

(65) Prior Publication Data
US 2016/0109442 A1 Apr. 21, 2016

(30) Foreign Application Priority Data

Dec. 15, 2010 (JP) ................ 2010-279005

(51) Int. Cl.
*G01N 33/564* (2006.01)
(52) U.S. Cl.
CPC ... *G01N 33/564* (2013.01); *G01N 2333/4703* (2013.01); *G01N 2800/102* (2013.01)
(58) Field of Classification Search
CPC ......... G01N 33/564; G01N 2333/4703; G01N 2800/102
See application file for complete search history.

(56) References Cited

U.S. PATENT DOCUMENTS

| 7,956,036 B2 * | 6/2011 | Sato | C07K 14/47 435/375 |
| 2005/0048574 A1 * | 3/2005 | Kantor | G01N 33/564 435/7.1 |
| 2005/0202421 A1 * | 9/2005 | Hirsch | C12Q 1/6883 435/6.14 |
| 2007/0148704 A1 | 6/2007 | Klause et al. | |
| 2010/0278837 A1 * | 11/2010 | Varner | C07K 16/40 424/158.1 |

FOREIGN PATENT DOCUMENTS

| JP | 2003-24099 A | 1/2003 |
| JP | 2004-12447 A | 1/2004 |
| JP | 2005-127754 A | 5/2005 |
| JP | 2009-510464 A | 3/2009 |
| JP | 2010-71833 A | 4/2010 |
| WO | 03/006985 A1 | 1/2003 |
| WO | 03072827 A1 | 9/2003 |
| WO | 2008089152 A2 | 7/2008 |
| WO | 2010115077 A2 | 10/2010 |

OTHER PUBLICATIONS

Plavina et al., 2008. Increased plasma concentrations of cytoskeletal and Ca2+-binding proteins and their peptides in psoriasis patients. Clin. Chem. 54: 1805-1814.*
Xiao et al., Jul. 8, 2010. Talin 2 concentrations in cerebrospinal fluid in patients with epilepsy. Clin. Biochem. 43: 1129-1132.*
Youns et al., 2013. Serum talin-1 is a potential novel biomarker for diagnosis of hepatocellular carcinoma in Egyptian patients. Asian Pacific J. Cancer Prev. 14: 3819-3823.*
Zheng et al., 2009. Study of the human plasma proteome of rheumatoid arthritis. J. Chromatog. A 1216: 3538-3545.*
Isenberg et al., Peptide-specific antibodies localize the major lipid binding sites of talin dimers to oppositely arranged N-terminal 47 dDa subdomains, FEBS Letters 426, 1998, pp. 165-170.*
Biodesign International, Monoclonal antibody to Human Talin (C-terminal specific), Specificatin Sheet, Jan. 26, 2006, p. 1.*
Bacakova et al: "Molecular mechanisms of improved adhesion and growth of an endothelial cell line cultured on polystyrene implanted with fluorine ions," Elsevier Science Publishers BV., Barking, GB, vol. 21, No. 11, Jun. 1, 2000, pp. 1173-1179.
Li T et al: "Over-expression of talin 1 and integrin-linked kinase in PBMCs of patients with ankylosing spondylitis: a proteomic study", Clinical and Experimental Rheumatology Nov.-Dec. 2010, vol. 28, No. 6, Nov. 2010 (Nov. 2010), pp. 828-835.
Li Tianwang et al, "Distinct Proteomic Profile in Ankylosing Spondylitis Patients: Talin1 is a New Valuable Biomarker for Diagnosis and Treatment," Arthritis & Rheumatism, vol. 58, No. 9, Suppl. S, Sep. 2008, pp. S350-S351.
Martin Schulz et al: "Proteomic Analysis of Peripheral Blood Mononuclear Cells: Selective Protein Processing Observed in Patients with Rheumatoid Arthritis", Journal of Proteome Research, vol. 6, No. 9, Sep. 1, 2007 (Sep. 1, 2007), pp. 3752-3759.
Notice of extended European search report issued to EP Application No. 11849351.9, mailed Aug. 26, 2014.
Tsuzaka et al: "Plasma Talin is a New Diagnostic and Monitoring Marker for Rheumatoid Arthritis", Arthritis & Rheumatism, vol. 63, No. 10, Suppl. S, Oct. 2011 (Oct. 2011), p. S134-S135.
Avouac J. et al., Diagnostic and predictive value of anti-cyclic citrullinated protein antibodies in rheumatoid arthritis: a systematic literature review, Ann. Rheum. Dis., 2006, vol. 65, pp. 845-851.

(Continued)

*Primary Examiner* — Gary W Counts
(74) *Attorney, Agent, or Firm* — Cantor Colburn LLP

(57) ABSTRACT

Provided are: a novel test method for rheumatoid arthritis; and a kit for rheumatoid arthritis test, which is used in the novel test method for rheumatoid arthritis. A test method for rheumatoid arthritis according to the present invention is characterized by comprising a step for measuring the amount of talin in the plasma or serum of an animal subject. This measurement is carried out, for example, by an immunological method using an antibody which binds to talin. A kit for rheumatoid arthritis test according to the present invention is used for such a test method and contains, for example, a solid-phase carrier to which an antibody that binds to talin is affixed.

18 Claims, 2 Drawing Sheets

(56) References Cited

OTHER PUBLICATIONS

International Search Report for International Application No. PCT/JP2011/063563, mailed Sep. 27, 2011, with English translation.
Van Boekel et al., Autoantibody systems in rheumatoid arthritis: specifity, sensitivity and diagnostic value, Arthritis Res., 2002, vol. 4, pp. 87-93.
Van Venrooij W.J. et al., Anti-CCP antibody, a marker for the early detection of rheumatoid arthritis, Ann. N. Y. Acad. Sci., 2008, vol. 1143, pp. 268-285.
Hajime Yoshifuji, "Calpain/Calpastatin to Rheumatoid Arthritis", Rinsho Rheumatism, Sep. 30, 2005 (Sep. 30, 2005), vol. 17, No. 3, pp. 160-165, Title only, no translation provided.
First Chinese Office Action to Chinese Patent Application No. 201180024137.5; Mailed Aug. 25, 2014, with English summary.

\* cited by examiner

TEST METHOD FOR RHEUMATOID ARTHRITIS AND KIT FOR RHEUMATOID ARTHRITIS TEST

CROSS REFERENCE TO RELATED APPLICATIONS

This is a U.S. national stage of application No. PCT/JP2011/063563, filed on 14 Jun. 2011. Priority under 35 U.S.C. §119(a) and 35 U.S.C. §365(b) is claimed from Japanese Application No. 2010-279005, filed 15 Dec. 2010, the disclosure of which are also incorporated herein by reference.

TECHNICAL FIELD

The present invention relates to a test method for rheumatoid arthritis, and a kit for rheumatoid arthritis test, which is used in such a test method.

BACKGROUND ART

Rheumatoid arthritis (RA) is a chronic inflammatory disease, in which the lesion occurs mainly in the synovial membrane tissue of the joint, and the prevalence rate of the disease is about 1% of the population. In rheumatoid arthritis, synovitis is found in the first stage, then cartilage or bone is gradually invaded, and the joint is destroyed and deformed in the advanced stage. Furthermore, the consequence of the symptom includes various examples such as an example in which arthritis undergoes remission and reoccurrence, repeatedly, then is completely cured, and an example in which arthritis rapidly progresses.

Diagnosis of rheumatoid arthritis is carried out mainly based on symptoms. Recently, however, attention has been paid to a diagnostic method using, as a marker, an autoantibody contained in the serum of a patient. As such an autoantibody, a rheumatoid factor (an autoantibody with respect to the deformed IgG), an anti-cyclic citrullinated peptide antibody (an anti-CCP antibody), and the like, are known (see Non-Patent Literature 1).

However, in previous reports, the sensitivity of the rheumatoid factor is 75 to 80%, the specificity thereof is 50 to 70%, and the sensitivity of the anti-CCP antibody is 50 to 75%, and the specificity is 85 to 95%, which are not necessarily satisfactory (see Non-Patent Literatures 2 and 3).
Non-Patent Literature 1: Martinus A. M. et al., Arthritis Res. Ther., 4: 87-93, 2002
Non-Patent Literature 2: Avouac J. et al., Ann. Rheum. Dis. 65: 845-851, 2006
Non-Patent Literature 3: van Venrooij W J. et al. Ann. N.Y. Acad. Sci. 1143: 268-285, 2008

DISCLOSURE OF THE INVENTION

Problems to be Solved by the Invention

The present invention aims to provide a test method for rheumatoid arthritis and a kit for rheumatoid arthritis test by searching novel markers that have not been previously known and being based on the found novel markers in the searching.

Means for Solving the Problems

In patients with rheumatoid arthritis, it is known that the peripheral blood lymphocyte is activated, so that cell adhesion with respect to the blood vessel endothelial cell is increased and at the same time, the lymphocyte migration is also increased, resulting in the infiltration of the lymphocyte to the outside of the blood vessel to cause various inflammations. In searching novel markers, the present inventor has focused on talin that is a high-molecular-weight cytoskeletal protein expressed in a concentrated manner mainly in regions in which the cell and the substrate are brought into contact with each other, in particular, in a cell adhesion region in the lymphocyte.

Talin is a protein formed of an N-terminal region having a molecular weight of 47 kDa and including an FERM region, and a C-terminal region having a molecular weight of 190 kDa and including one bundle of α-helix. The FERM region is classified into three sub-regions, that is, an F1 domain, an F2 domain, and an F3 domain, sequentially from the N-terminal side. In a living body, it is known that polypeptide in the N-terminal region, which is cleaved by Calpain, the F3 domain among them binds to an integrin β sub-unit increases signaling of the integrin from the inside of the cell to the outside of the cell, and thus the cell adhesion and cell migration are increased.

The present inventor has investigated the presence of talin in the plasma or the serum of a patient with rheumatoid arthritis. As a result, surprisingly, it is found that in a patient with rheumatoid arthritis, talin is dominantly present in the plasma or the serum. Furthermore, it is found that the amount of talin is significantly reduced when rheumatoid arthritis reaches a low disease activity or remission with the therapeutic agent for rheumatoid arthritis.

The present invention has been made based on such findings, and the present invention specifically includes the followings.

(1) A test method for rheumatoid arthritis, the method including a step of measuring an amount of talin in plasma or serum of an animal subject.

(2) The test method for rheumatoid arthritis described in the above (1), further including a step of obtaining plasma or serum from blood collected from the animal subject.

(3) The test method for rheumatoid arthritis described in the above (1) or (2), wherein the amount of talin in the plasma or the serum is measured by using an antibody which binds to talin.

(4) The test method for rheumatoid arthritis described in any of the above (1) to (3), wherein the animal subject is a human subject.

(5) The test method for rheumatoid arthritis described in any of the above (1) to (4), wherein the method is carried out for determining a diagnosis of rheumatoid arthritis or a treatment effect of a therapeutic agent for rheumatoid arthritis.

(6) A kit for rheumatoid arthritis test used for the test method for rheumatoid arthritis described in any of the above (1) to (5).

(7) The kit for rheumatoid arthritis test described in the above (6), including a solid-phase carrier to which an antibody that binds to talin is affixed.

Effects of the Invention

The present invention can provide a novel test method for rheumatoid arthritis and a kit for rheumatoid arthritis test to be used for such a test method.

PREFERRED MODE FOR CARRYING OUT THE INVENTION

Test Method for Rheumatoid Arthritis

Figure 1:
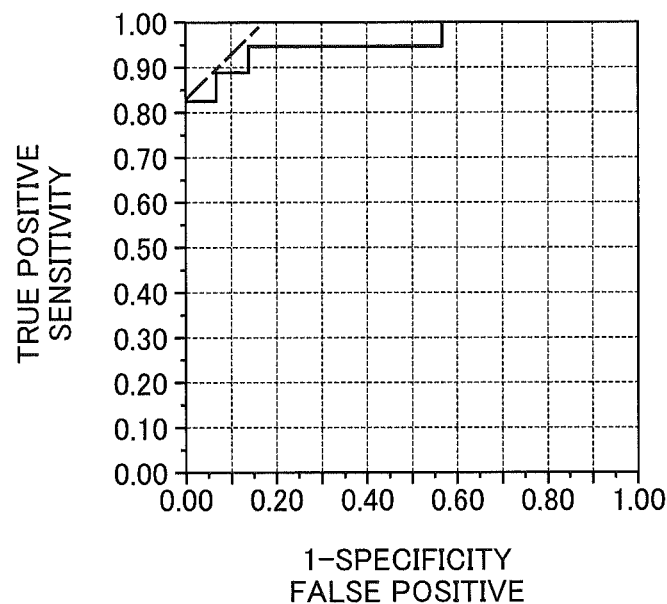
FIG. 1 is a graph showing an ROC curve of a diagnosis of rheumatoid arthritis (Example 1) by the Sandwich ELISA method using an H-18 antibody and an H-300 antibody.

A test method for rheumatoid arthritis according to the present invention includes a step of measuring an amount of talin in the plasma or the serum of an animal subject. This test method may further include a step of obtaining the plasma or the serum from the blood collected from an animal subject.

The animal subject is not particularly limited as long as it can contract rheumatoid arthritis, and it can be selected depending upon purposes. Examples thereof include a human, a rat, a mouse, a dog, a cow, a cat, a rabbit, and a guinea pig, and preferable example is a human.

Furthermore, a method for obtaining the plasma or the serum is not particularly limited, it is possible to employ conventional methods, for example, a method for separating the plasma or the serum, which are obtained as specimen for clinical laboratory examination, from the blood. For example, the plasma can be obtained by taking the blood into an EDTA tube, a heparin tube, or the like, and the centrifuging thereof. Furthermore, the serum can be obtained by taking the blood into a test tube, and the centrifuging thereof.

With the test method for rheumatoid arthritis according to the present invention, an amount of talin in the thus obtained plasma or serum is measured. Herein, the "amount of talin" denotes an amount of protein of the talin. When talin has plurality of isoforms, any one of them may be measured. For example, in the case of human, two isoforms, that is, talin 1 and talin 2 are present. The mRNA sequence and the amino acid sequence of the talin 1 are shown in SEQ ID NOs: 1 and 2. Furthermore, the mRNA sequence and the amino acid sequence of the talin 2 are shown in SEQ ID NOs: 3 and 4.

The amount of talin in the plasma or the serum of an animal subject can be measured by an immunochemical method by using an antibody which binds to talin.

The antibody which binds to talin may be a polyclonal antibody or may be a monoclonal antibody, and, in some case, fragments of the antibody, for example, Fab', Fab, F(ab')$_2$ can be used. These antibodies can be prepared by conventionally known methods.

Examples of commercial products include an H-18 antibody (Santa Cruz Biotechnology Inc.), an H-300 antibody (Santa Cruz Biotechnology Inc.), a TA205 antibody (Abcam Inc.), and an M54246M antibody (Bio-design Co., Ltd.).

The amount of talin can be measured by employing well-known methods such as an enzyme immunoassay (EIA), a chemiluminescent immunoassay, a radioimmunoassay (RIA), a fluoro immunoassay, and a latex agglutination assay. Specific examples include a competitive assay using an antibody and label antigen, a Sandwich EIA method using combination of two types of antibodies, i.e., a monoclonal antibody or a polyclonal antibody (or a monoclonal antibody and a polyclonal antibody) whose recognition sites with respect to an antigen are different, and a latex agglutination assay using latex particles to which an antibody is affixed.

In these measurement methods, if necessary, an antigen or an antibody can be affixed to a solid-phase carrier. Examples of the solid-phase carrier include synthetic resin such as polystyrene, polyethylene, polypropylene, polyvinyl chloride, polyester, polyacrylic acid ester, nylon, polyacetal and fluorocarbon resin, polysaccharides such as cellulose and agarose, glass, metal, and the like. This solid-phase carrier can be formed in various shapes including a micro-plate shape, a spherical shape, a fibrous shape, a rod shape, a board shape, a container shape, a cell, a test tube, and the like.

In the above-mentioned immunochemical method, antibodies or antigens which are labeled may be used if necessary. Examples of such labels include radioisotope ($^{124}$I, $^{14}$C, and $^{3}$H), fluorescence materials (fluorescein isothiocyanate, and the like), and the like, in addition to enzymes (peroxidase, alkaline phosphatase, and the like), luminescent material (acridinium ester, isoluminol, luciferin, and the like). Besides, methods using combination of a biotin label and streptavidin can be employed.

As mentioned above, by measuring and quantifying the amount of talin in the plasma or the serum of an animal subject, it is possible to diagnose easily whether or not the subject has contracted rheumatoid arthritis. That is to say, when the amount of talin in the plasma or the serum is larger than a predetermined threshold, it can be determined that the subject has contracted rheumatoid arthritis. The predetermined threshold can be set, for example, based on a mean value and the like in the plasma or the serum in a control animal that has not contracted rheumatoid arthritis.

Furthermore, by measuring and quantifying the amount of talin before and after a therapeutic agent for rheumatoid arthritis is administered, a therapeutic effect by the therapeutic agent can be determined in a simple and easy manner. That is to say, when the amount of talin after the therapeutic agent for rheumatoid arthritis is administered is significantly lowered from the amount of talin before the administration, it can be determined that the therapeutic agent is effective.

Herein, the therapeutic agent for rheumatoid arthritis can include all the conventionally known therapeutic agents and all of therapeutic agents that will be developed in the future. Examples of the conventionally known therapeutic agent for rheumatoid arthritis include biological preparations, non-steroidal anti-inflammatory agents (anti-inflammatory analgesic agents), steroid drugs, immunosuppressive agents, and the like.

Examples of the biological preparations include chimeric anti-TNF-α antibody preparations, soluble TNF receptors, complete human anti-TNF-α antibody preparations, anti-IL-6-receptor antibody preparations, and the like. The non-steroidal anti-inflammatory agents include prostaglandin production suppressing agents. They can reduce pain or swelling in the joint, but it is said that it is difficult to suppress the progress of the disease itself and suppress the destruction of the bone and the joint. The steroid drug has excellent anti-inflammation effect, so that it is used as specific medicine for rheumatoid arthritis. However, adverse effects thereof pose problems. The immunosuppressive agent reduces immunopathy of a rheumatoid arthritis patient, thereby suppressing the inflammation of rheumatoid arthritis, and is used for the purpose of introducing remission induction. Since this may be able to inhibit the progress of rheumatoid arthritis, this agent is also called disease modification anti-rheumatism drug. This is also called a slow acting anti-rheumatism drug because it takes a long time to exhibit an effect.

As mentioned above, there are various types of the therapeutic agents for rheumatoid arthritis, but the test method according to the present invention is also useful for determining the level of the effect of the therapeutic agent, and selecting the most effective therapeutic agent.

Kit for Rheumatoid Arthritis Test

A kit for rheumatoid arthritis test according to the present invention is provided for the use in a test method for rheumatoid arthritis according to the present invention. This diagnosis kit includes, for example, a solid-phase carrier to which an antibody that binds to talin is affixed. Furthermore, it may include a labeled secondary antibody, a coloring substrate, or the like.

EXAMPLES

Hereinafter, the present invention is described in detail with reference to Examples, but the present invention is not construed as being limited to the following description. Note here that in the following Examples 1 and 2, and Comparative Example 1, subjects include 17 patients with rheumatoid arthritis (RA patients), 14 controls (8 patients with osteoarthritis, 1 patient with systemic lupus erythematodes, 1 patient with diabetes, and 4 healthy subjects). Furthermore, in the following Example 3, subjects are 5 RA patients.

Example 1

Blood of each subject is collected into an EDTA tube, and is centrifuged at 2500 rpm at room temperature for 10 min so as to obtain the plasma.

An amount of talin in the plasma was measured by a Sandwich ELISA method.

Firstly, an H-18 antibody (Santa Cruz Biotechnology Inc.) recognizing the N-terminal of talin was diluted with a phosphate buffer solution (PBS) so that the concentration became 1 µg/mL, and added to a 96-well micro-plate at 100 µL/well, which was incubated at 4° C. overnight, followed by washing with 200 µL/well of washing solution three times. Next, the plasma from each subject was added to the 96-well micro-plate at 100 µL/well, which was incubated at 25° C. for one hour, followed by washing with 200 µL/well of washing solution three times. Next, an H-300 antibody (Santa Cruz Biotechnology Inc.) as a primary antibody recognizing the N-terminal of talin was diluted with PBS so that the concentration became 2 µg/mL, and added to the 96-well micro-plate at 100 µL/well, which was incubated at 25° C. for one hour, followed by washing with 200 µL/well of washing solution three times. Next, an HRP-labeled anti-goat IgG antibody (KPL) as a secondary antibody was diluted with PBS so that the concentration became 2 µg/mL, and added to the 96-well micro-plate at 100 µL/well, which was incubated at 25° C. for one hour, followed by washing with 200 µL/well of washing solution three times.

Next, a substrate was added to a 96-well micro-plate at 100 µL/well, which was incubated at 25° C. for 15 min, and then, an OD value at wavelength of 630 nm was measured by using a microplate reader.

An ROC curve in Example 1 is shown in FIG. 1. As a result of the ROC analysis, an area below the ROC curve (AUC) in FIG. 1 was 0.954. Furthermore, whether being positive or negative based on the cut-off value of OD=0.20 is shown in Table 1.

TABLE 1

|  |  | RA patient | Control | Total |
|---|---|---|---|---|
| H-300 antibody | Positive | 14 | 0 | 14 |
|  | Negative | 3 | 14 | 17 |
|  | Total | 17 | 14 | 31 |

From the results, diagnosis of rheumatoid arthritis by the Sandwich ELISA method using the H-18 antibody and the H-300 antibody showed that the sensitivity was 14/17×100=82.4% and the specificity was 14/14×100=100%.

Example 2

The amount of talin in the plasma was measured by the Sandwich ELISA method by the same method as in Example 1 except that an M54246M antibody (Bio-design Co., Ltd.) recognizing the C-terminal of talin was used as a primary antibody.

Figure 2:
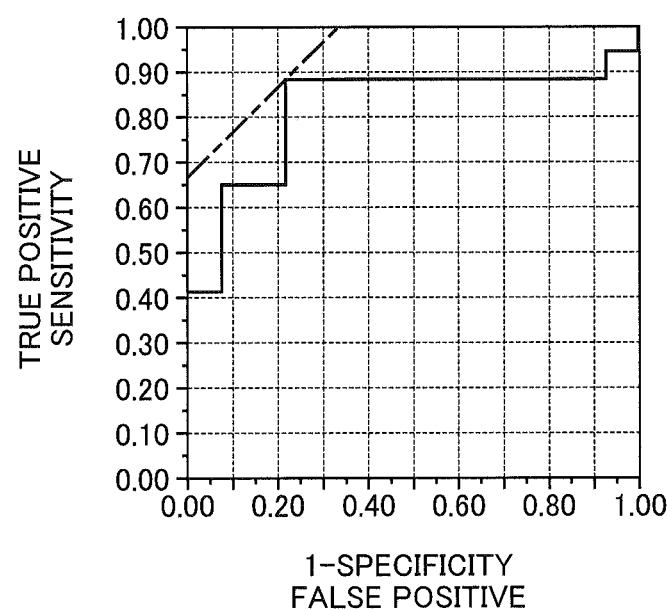
FIG. 2 is a graph showing an ROC curve of a diagnosis of rheumatoid arthritis (Example 2) by the Sandwich ELISA method using an H-18 antibody and an M54246M antibody.

An ROC curve in Example 2 is shown in FIG. 2. As a result of the ROC analysis, an area below the ROC curve (AUC) in FIG. 2 was 0.819. Furthermore, whether being positive or negative based on the cut-off value of OD=0.05 is shown in Table 2.

TABLE 2

|  |  | RA patient | Control | Total |
|---|---|---|---|---|
| M54246M antibody | Positive | 15 | 3 | 18 |
|  | Negative | 2 | 11 | 13 |
|  | Total | 17 | 14 | 31 |

From the results, diagnosis of rheumatoid arthritis by the Sandwich ELISA method using the H-18 antibody and the M54246M antibody showed that the sensitivity was 15/17×100=88.2% and the specificity was 11/14×100=78.6%.

Comparative Example 1

Blood from each subject was collected into a blood collecting tube for serum, and it was centrifuged at 2,500 rpm at room temperature for 10 min, and thus the serum was obtained. An anti-CCP antibody titer in the serum was measured by using a commercially available kit (MESA-CUP CCP manufactured by Medical & Biological laboratories Co., Ltd (MBL)).

Figure 3:
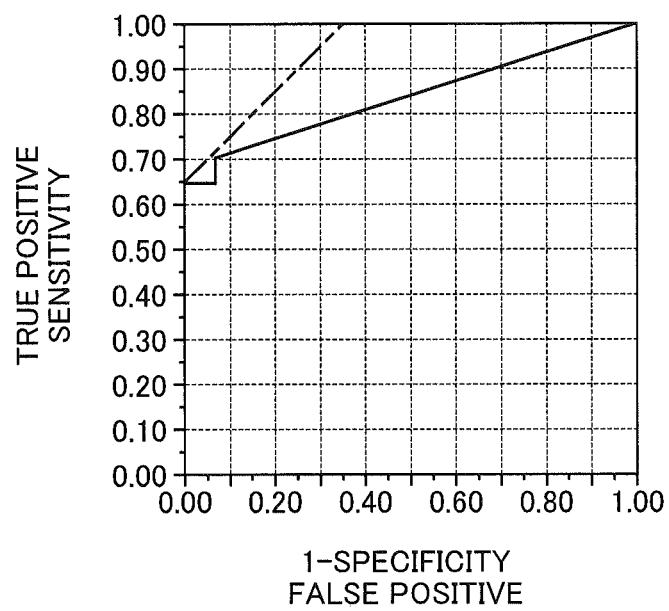
FIG. 3 is a graph showing an ROC curve of a diagnosis of rheumatoid arthritis (Comparative Example 1) using an anti-CCP antibody.

An ROC curve in Comparative Example 1 is shown in FIG. 3. As a result of the ROC analysis, an area below the ROC curve (AUC) in FIG. 3 was 0.838. Furthermore, whether being positive or negative based on the cut-off value of antibody titer=6.60 is shown in Table 3.

TABLE 3

|  |  | RA patient | Control | Total |
|---|---|---|---|---|
| Anti-CCP antibody | Positive | 11 | 1 | 12 |
|  | Negative | 6 | 13 | 19 |
|  | Total | 17 | 14 | 31 |

From the results, diagnosis of rheumatoid arthritis by using the anti-CCP antibody showed that the sensitivity was 11/17×100=64.7% and the specificity was 13/14×100=92.9%.

As is shown from the above-mentioned results, talin was dominantly present in the blood from a RA patient. Therefore, by measuring the amount of talin in the blood, it is possible to examine whether or not a subject contracted rheumatoid arthritis in a simple and easy manner. Moreover, the test method was more excellent in the sensitivity as compared with the existing method using anti-CCP antibody.

Example 3

A therapeutic effect of the therapeutic agent for rheumatoid arthritis for 5 RA patients was confirmed by measuring the amount of talin. The amount of talin was measured by measuring the OD value by the Sandwich ELISA method by using an H-18 antibody and an H-300 antibody as in Example 1. Furthermore, an amount of CRP and an amount of MMP-3 were measured by the same method as in usual clinical examination. Furthermore, the score of DAS (Disease Activity Score) 28 recommended by European League Against Rheumatism (EULAR) was calculated. The score of DAS28 of not less than 5.1 is determined to be high disease activity, the score of not less than 3.2 and less than 5.1 is determined to be middle disease activity, and the score of less than 3.2 is determined to be low disease activity. The results are shown in Table 4.

TABLE 4

| | | Before (MTX treatment) | After (MTX + ADA treatment) |
|---|---|---|---|
| Case 1: Male (ADA remarkable effective example) | Talin (OD value) | 0.568 | 0.139 |
| | CRP (mg/dL) | 1.74 | 0.08 |
| | MMP-3 (mg/mL) | 60.6 | 57.4 |
| | DAS28 | 5.43 | 2.62 |

| | | Before (non-treatment) | After (SASP treatment) |
|---|---|---|---|
| Case 2: Female (SASP no effective example) | Talin (OD value) | 0.258 | 0.294 |
| | CRP (mg/dL) | 0.36 | 0.19 |
| | MMP-3 (mg/mL) | 70.6 | 106.6 |
| | DAS28 | 5.12 | 4.21 |

| | | Before (MTX treatment) | After (MTX + IFX treatment) |
|---|---|---|---|
| Case 3: Female (IFX no effective example) | Talin (OD value) | 0.205 | 0.223 |
| | CRP (mg/dL) | 2.82 | 2.68 |
| | MMP-3 (mg/mL) | 962.1 | 523.8 |
| | DAS28 | 4.87 | 3.95 |

TABLE 4-continued

| | | Before (BUC treatment) | After (BUC + ADA treatment) |
|---|---|---|---|
| Case 4: Female (ADA remarkable effective example) | Talin (OD value) | 0.258 | 0.164 |
| | CRP (mg/dL | 5.01 | 0.16 |
| | MMP-3 (mg/mL) | 323.2 | 52.2 |
| | DAS28 | 4.55 | 2.45 |

| | | Before (non-treatment) | After (TCZ treatment) |
|---|---|---|---|
| Case 5: Female (TCZ no effective example) | Talin (OD value) | 2.093 | 1.787 |
| | CRP (mg/dL) | 3.83 | 2.78 |
| | MMP-3 (mg/mL) | 117.8 | 93.1 |
| | DAS28 | 5.09 | 4.50 |

A case 1 is an example in which when ADA (adalimumab) was used together in treatment with MTX (methotrexate), good responder (DAS28: 5.43→2.62) was shown based on the reactivity basis of EULAR. The amount of talin showed a high value (OD value: 0.568) when only MTX was used, but it showed a normal value (OD value: 0.139) when ADA was used together. On the other hand, the amount of MMP-3 did not show significant reduction even when ADA was used together, which did not reflect the activity of rheumatoid arthritis.

A case 2 is an example in which also when treatment with SASP (salazosuffapyridine) was carried out, none responder (DAS28: 5.12→4.21) was shown based on the reactivity basis of EULAR. The amount of talin remained high (OD value: 0.258→0.294) even with SASP treatment. On the other hand, the CRP amount showed a normal value (0.19 mg/dL) after the SASP treatment was carried out, which did not reflect the pathology of rheumatoid arthritis.

A case 3 is an example in which none responder (DAS28: 4.87→3.95) was shown although IFX (infliximab) was used together with treatment with MTX (methotrexate). The amount of talin remained high (OD value: 0.205→0.223) even when treatment together with IFX was carried out.

A case 4 is an example in which good responder (DAS28: 4.55→2.45) was shown when ADA (adalimumab) was used together with treatment with BUC (bucillamine). The amount of talin showed a high value (OD value: 0.258) when only BUC was used, but it showed a normal value (OD value: 0.164) when ADA was used together.

A case 5 is an example in which none responder (DAS28: 5.09→4.50) was shown also when treatment using TCZ (tocilizumab) was carried out. The amount of talin remained high (OD value: 2.093→1.787) even with TCZ treatment.

As is shown from the above-mentioned results, the amount of talin in the blood correlates with the activity of rheumatoid arthritis, and it reflects the activity of rheumatoid arthritis more precisely as compared with the other factors such as CRP and MMP-3. Therefore, by measuring the amount of talin in the blood, it is possible to precisely determine the therapeutic effect of a therapeutic agent for rheumatoid arthritis.

The invention claimed is:

1. A test method for diagnosing rheumatoid arthritis, the method comprising:

measuring an amount of talin in plasma or serum of an animal subject by causing an H-18 antibody and an H-300 antibody to bind to talin, or by causing an H-18 antibody and an M54246M antibody to bind to talin; and diagnosing that the animal subject has contracted rheumatoid arthritis when the amount of talin thus measured is found to be larger than a predetermined threshold.

2. The test method for diagnosing rheumatoid arthritis according to claim 1, further comprising obtaining the plasma or the serum from blood collected from the animal subject.

3. The test method for diagnosing rheumatoid arthritis according to claim 1, wherein the animal subject is a human subject.

4. The test method for diagnosing rheumatoid arthritis according to claim 1, further comprising determining a treatment effect of a therapeutic agent for rheumatoid arthritis.

5. A kit for rheumatoid arthritis test comprising an H-18 antibody and an H-300 antibody, or an H-18 antibody and an M54246M antibody.

6. The test method for diagnosing rheumatoid arthritis according to claim 1, wherein the predetermined threshold is based on a mean value in the plasma or the serum in a control animal that has not contracted rheumatoid arthritis.

7. The test method for diagnosing rheumatoid arthritis according to claim 1, wherein the amount of talin in the plasma or the serum is measured by a Sandwich ELISA method employing the H-18 antibody and the H-300 antibody.

8. The test method for diagnosing rheumatoid arthritis according to claim 1, wherein the amount of talin in the plasma or the serum is measured by a Sandwich ELISA method employing the H-18 antibody and the M54246M antibody.

9. A test method for determining a treatment effect of a therapeutic agent for rheumatoid arthritis, the method comprising:
measuring an amount of talin in plasma or serum of an animal subject by causing an antibody to bind to talin after the therapeutic agent is administered to the animal subject, wherein the antibody is an H-18 antibody and an H-300 antibody, or an H-18 antibody and an M54246M antibody; and
determining that the therapeutic agent is effective when the amount of talin thus measured is found to be significantly lowered from an amount of talin in plasma or serum of the animal subject before the administration.

10. The test method for determining a treatment effect of a therapeutic agent for rheumatoid arthritis according to claim 9, further comprising obtaining the plasma or the serum from blood collected from the animal subject.

11. The test method for determining a treatment effect of a therapeutic agent for rheumatoid arthritis according to claim 9, wherein the animal subject is a human subject.

12. The test method for determining a treatment effect of a therapeutic agent for rheumatoid arthritis according to claim 9, wherein the amount of talin in the plasma or the serum is measured by a Sandwich ELISA method employing the H-18 antibody and the H-300 antibody.

13. The test method for determining a treatment effect of a therapeutic agent for rheumatoid arthritis according to claim 9, wherein the amount of talin in the plasma or the serum is measured by a Sandwich ELISA method employing the H-18 antibody and the M54246M antibody.

14. The test method for diagnosing rheumatoid arthritis according to claim 1, wherein the H-18 antibody and the H-300 antibody, or the H-18 antibody and the M54246M antibody are comprised in a kit.

15. The test method for diagnosing rheumatoid arthritis according to claim 1, wherein either one of the H-18 antibody or the H-300 antibody, or either one of the H-18 antibody or the M54246M antibody is affixed to a solid-phase carrier.

16. The test method for diagnosing rheumatoid arthritis according to claim 1, wherein the H-18 antibody is affixed to a solid-phase carrier.

17. The kit for rheumatoid arthritis test according to claim 5, further comprising a solid-phase carrier to which either one of the H-18 antibody or the H-300 antibody, or either one of the H-18 antibody or the M54246M antibody is affixed.

18. The kit for rheumatoid arthritis test according to claim 5, further comprising a solid-phase carrier to which the H-18 antibody is affixed.

* * * * *

SEQUENCE LISTING

<160> NUMBER OF SEQ ID NOS: 4

<210> SEQ ID NO 1
<211> LENGTH: 8187
<212> TYPE: DNA
<213> ORGANISM: Homo sapiens

<400> SEQUENCE: 1

```
cccgagaagc ggcggggcgg cgggccggcg ggcggggcgc agagccaggc agcgcaggta      60
tagccaggct ggagaaaaga agctgccacc atggttgcac tttcactgaa gatcagcatt     120
gggaatgtgg tgaagacgat gcagtttgag ccgtctacca tggtgtacga cgcctgccgc     180
atcattcgtg agcggatccc agaggcccca gctggtcctc ccagcgactt ggggctcttt     240
ctgtcagatg atgaccccaa aaagggtata tggctggagg ctgggaaagc tttggactac     300
tacatgctcc gaaatgggga cactatggag tacaggaaga acagagaccc ctgaagatc      360 cgtatgctgg atgaactgt gaagacgatc atggtggatg actctaagac tgtcactgac     420
atgctcatga ccatctgtgc ccgcattggc atcaccaatc atgatgaata ttcattggtt     480
cgagagctga tggaagagaa aaaggaggaa ataacaggga ccttaagaaa ggacaagaca     540
ttgctgcgag atgaaaagaa gatggagaaa ctaaagcaga aattgcacac agatgatgag     600
ttgaactggc tggaccatgg tcggacactg agggagcagg gtgtagagga gcacgagacg     660
ctgctgctgc ggaggaagtt cttttactca gaccagaatg tggattcccg ggaccctgta     720
cagctgaacc tcctgtatgt gcaggcacga gatgacatcc tgaatggctc ccaccctgtc     780
tcctttgaca aggcctgtga gtttgctggc ttccaatgcc agatccagtt tgggccccac     840
aatgagcaga agcacaaggc tggcttcctt gacctgaagg acttcctgcc caaggagtat     900
gtgaagcaga agggagagcg taagatcttc caggcacaca agaattgtgg gcagatgagt     960
gagattgagg ccaaggtccg ctacgtgaag ctagcccgtt ctctcaagac ttacggtgtc    1020
tccttcttcc tggtgaagga aaaaatgaaa gggaagaaca agctagtgcc caggcttctg    1080
ggcatcacca aggagtgtgt gatgcgagtg gatgagaaga ccaaggaagt gatccaggag    1140
tggaacctca ccaacatcaa acgctgggct gcgtctccca aaagcttcac cctggatttt    1200
ggagattacc aagatggcta ttactcagta cagacaactg aaggggagca gattgcacag    1260
ctcattgccg gctacatcga tatcatcctg aagaagaaaa aaagcaagga tcactttggg    1320
ctggaaggag atgaggagtc tactatgctg gaggactcag tgtcccccaa aaagtcaaca    1380
gtcctgcagc agcaatacaa ccgggtgggg aaagtggagc atggctctgt ggccctgcct    1440
gccatcatgc gctctggagc ctctggtcct gagaatttcc aggtgggcag catgcccccc    1500
gcccagcagc agattaccag cggccagatg caccgaggac acatgcctcc tctgacttca    1560
gcccagcagg cactcactgg aaccattaac tccagcatgc aggccgtgca ggctgcccag    1620
gccaccctgg atgactttga cactctgccg cctcttggcc aggatgctgc ctctaaggcc    1680
tggcgtaaaa acaagatgga tgaatcaaag catgagatcc actctcaggt agatgccatc    1740
acagctggta ctgcgtctgt ggtgaacctg acagcagggg accctgctga cagagactat    1800
accgcagtgg gctgtgcagt caccacaatc tcctccaacc tgacggagat gtcccgtggg    1860
gtgaagctgc tggctgcctt gctggaggac gaaggcggca gtggtcggcc cctgttgcag    1920
gcagcaaagg gccttgcggg agcagtgtca gaactgctgc gcagtgccca accagccagt    1980
gctgagcccc gtcagaacct gctgcaagca gctgggaacg tgggccaggc cagtggggag    2040
ctgttgcaac aaattgggga agtgatact gaccccccact tccaggatgc gctaatgcag    2100
ctcgccaaag ctgtggcaag tgctgcagct gccctggtcc tcaaggccaa gagtgtggcc    2160
cagcggacag aggactcggg acttcagacc caagttattg ctgcagcaac acagtgtgcc    2220
ctatccactt cccaactagt ggcctgtact aaggtggtgg cacctacaat cagctcacct    2280
gtctgccaag agcaactggt ggaggctgga cgactggtag ccaaagccgt ggagggctgt    2340
```

```
gtgtctgcct cccaggcagc tacagaggat gggcaactgt tgcgaggggt aggagcagca    2400
gccacagctg tcacccaggc cctaaatgag ctgctgcagc atgtgaaagc ccatgccaca    2460
ggggctgggc ctgctggccg ttatgaccag gctactgaca ccatcctaac cgtcactgag    2520
aacatcttta gctccatggg tgatgctggg gagatggtgg gacaggcccg catcctggcc    2580
caagccacat ctgacctggt caatgccatc aaggctgatg ctgaggggga aagtgatctg    2640
gagaactccc gcaagctctt aagtgctgcc aagatcctag ctgatgccac agccaagatg    2700
gtagaggctg ccaagggagc agctgcccac cctgacagtg aggagcagca gcagcggctg    2760
cgggaggcag ctgaggggct gcgcatggcc accaatgcag ctgcgcagaa tgccatcaag    2820
aaaaagctgg tgcagcgcct ggagcatgca gccaagcagg ctgcagcctc agccacacag    2880
accatcgctg cagctcagca cgcagcctct accccaaag cctctgccgg cccccagccc    2940
ctgctggtgc agagctgcaa ggcagtggca gagcagattc cactgctggt gcagggcgtc    3000
cgaggaagcc aagcccagcc tgacagcccc agcgctcagc ttgccctcat tgctgccagc    3060
cagagcttcc tgcagccagg tgggaagatg gtggcagctg caaaggcctc agtgccaacg    3120
attcaggacc aggcttcagc catgcagctg agtcagtgtg ccaagaacct gggcaccgcg    3180
ctggctgaac tccggacggc tgcccagaag gctcaggaag catgtggacc tttggagatg    3240
gattctgcac tgagtgtggt acagaatcta gagaaagatc tacaggaagt gaaggcagca    3300
gctcgagatg gcaagcttaa acccttacct ggggagacaa tggagaagtg tacccaggac    3360
ctgggcaaca gcaccaaagc cgtgagctca gccatcgccc agctactggg agaggttgcc    3420
cagggcaatg agaattatgc aggtattgca gctcgggatg tggcaggtgg gctgcggtca    3480
ctggcccagg ccgctagggg agtcgctgca ctgacgtcag atcctgcagt gcaggccatt    3540
gtacttgata cggccagtga tgtgctggac aaggccagca gcctcattga ggaggcgaaa    3600
aaggcagctg ccatccagg ggaccctgag agccagcagc ggcttgccca ggtggctaaa    3660
gcagtgaccc aggctctgaa ccgctgtgtc agctgcctac ctggccagcg cgatgtggat    3720
aatgccctga gggcagttgg agatgccagc aagcgactcc tgagtgactc gcttcctcct    3780
agcactggga catttcaaga agctcagagc cggttgaatg aagctgctgc tgggctgaat    3840
caggcagcca cagaactggt gcaggcctct cggggaaccc ctcaggacct ggctcgagcc    3900
tcaggccgat ttggacagga cttcagcacc ttcctggaag ctggtgtgga gatgcaggc    3960 caggctccga gccaggagga ccgagcccaa gttgtgtcca acttgaaggg catctccatg    4020
tcttcaagca aacttcttct ggctgccaag gccctgtcca cggaccctgc tgcccctaac    4080
ctcaagagtc agctggctgc agctgccagg gcagtaactg acagcatcaa tcagctcatc    4140
actatgtgca cccagcaggc acccggccag aaggagtgtg ataacgccct gcgggaattg    4200
gagacggtcc gggaactcct ggagaaccca gtccagccca tcaatgacat gtcctacttt    4260
ggttgcctgg acagtgtaat ggagaactca aaggtgctgg gcgaggccat gactggcatc    4320
tcccaaaatg ccaagaacgg aaacctgcca gagtttggag atgccatttc cacagcctca    4380
aaggcacttt gtggcttcac cgaggcagct gcacaggctg catatctggt tggtgtctct    4440
gaccccaata gccaagctgg acagcaaggg ctagtggagc ccacacagtt tgcccgtgca    4500
aaccaggcaa ttcagatggc ctgccagagt ttgggagagc ctggctgtac ccaggcccag    4560
gtgctctctg cagccaccat tgtggctaaa cacacctctg cactgtgtaa cagctgtcgc    4620
ctggcttctg cccgtaccac caatcctact gccaagcgcc agtttgtaca gtcagccaag    4680
gaggtggcca acagcacagc taatcttgtc aagaccatca aggcgctaga tgggccttc    4740
```

```
acagaggaga accgtgccca gtgccgagca gcaacagccc ctctgctgga ggctgtggac    4800
aatctgagtg cctttgcgtc caaccctgag ttctccagca ttcctgccca gatcagccct    4860
gagggtcggg ctgccatgga gcccattgtg atctctgcca agacaatgtt agagagtgcc    4920
gggggactca tccagacagc ccgggccctc gcagtcaatc cccgggaccc ccgagctgg     4980
tcggtgctgg ccggccactc ccgtactgtc tcagactcca tcaagaagct aattacaagc    5040
atgagggaca aggctccagg gcagctggag tgtgaaacgg ccattgcagc tctgaacagt    5100
tgtctacggg acctagacca ggcttccctc gctgcagtca gccagcagct tgctccccgt    5160
gagggaatct ctcaagaggc cttgcacact cagatgctca ctgcagtcca agagatctcc    5220
catctcattg agccgctggc caatgctgcc cgggctgaag cctcccagct gggacacaag    5280
gtgtcccaga tggcgcagta ctttgagccg ctcaccctgg ctgcagtggg tgctgcctcc    5340
aagaccctga gccacccgca gcagatggca ctcctggacc agactaaaac attggcagag    5400
tctgccctgc agttgctata cactgccaag gaggctggtg gtaacccaaa gcaagcagct    5460
cacacccagg aagccctgga ggaggctgtg cagatgatga ccgaggccgt agaggacctg    5520
acaacaaccc tcaacgaggc agccagtgct gctggggtcg tgggtggcat ggtggactcc    5580
atcacccagg ccatcaacca gctagatgaa ggaccaatgg gtgaaccaga aggttccttc    5640
gtggattacc aaacaactat ggtgcggaca gccaaggcca ttgcagtgac cgttcaggag    5700
atggttacca agtcaaacac cagcccagag gagctgggcc ctcttgctaa ccagctgacc    5760
agtgactatg ccgtctggc ctcggaggcc aagcctgcag cggtggctgc tgaaaatgaa     5820
gagataggtt cccatatcaa acaccgggta caggagctgg ccatggctg tgccgctctg     5880
gtcaccaagg caggcgccct gcagtgcagc cccagtgatg cctacaccaa gaaggagctc    5940
atagagtgtg cccggagagt ctctgagaag gtctcccacg tcctggctgc gctccaggct    6000
gggaatcgtg gcacccaggc ctgcatcaca gcagccagcg ctgtgtctgg tatcattgct    6060
gacctcgaca ccaccatcat gttcgccact gctggcacgc tcaatcgtga gggtactgaa    6120
actttcgctg accaccggga gggcatcctg aagactgcga aggtgctggt ggaggacacc    6180
aaggtcctgg tgcaaaacgc agctgggagc caggagaagt tggcgcaggc tgcccagtcc    6240
tccgtggcga ccatcacccg cctcgctgat gtggtcaagc tgggtgcagc cagcctggga    6300
gctgaggacc ctgagaccca ggtggtacta atcaacgcag tgaaagatgt agccaaagcc    6360
ctgggagacc tcatcagtgc aacgaaggct gcagctggca agttggagat gaccctgct     6420
gtgtggcagc taaagaactc tgccaaggtg atggtgacca atgtgacatc attgcttaag    6480
acagtaaaag ccgtggaaga tgaggccacc aaaggcactc gggccctgga ggcaaccaca    6540
gaacacatac ggcaggagct ggcggttttc tgttccccag agccaccgc caagacctct     6600
accccagaag acttcatccg aatgaccaag ggtatcacca tggcaaccgc caaggccgtt    6660
gctgctggca attcctgtcg ccaggaagat gtcattgcca cagccaatct gagccgccgt    6720
gctattgcag atatgcttcg ggcttgcaag gaagcagctt accacccaga agtggcccct    6780
gatgtgcggc ttcgagccct gcactatggc cgggagtgtg ccaatggcta cctggaactg    6840
ctggaccatg tactgctgac cctgcagaag ccaagcccag aactgaagca gcagttgaca    6900
ggacattcaa agcgtgtggc tggttccgtc actgagctca tccaggctgc tgaagccatg    6960
aagggaacaa aatgggtaga cccagaggac cccacagtca ttgctgagaa tgagctcctg    7020
ggagctgcag ccgccattga ggctgcagcc aaaaagctag agcagctgaa gccccgggcc    7080
```

```
aaacccaagg aggcagatga gtccttgaac tttgaggagc agatactaga agctgccaag      7140
tccattgcag cagccaccag tgcactggta aaggctgcgt cggctgccca gagagaacta      7200
gtggcccaag ggaaggtggg tgccattcca gccaatgcac tggacgatgg gcagtggtcc      7260
cagggcctca tttctgctgc ccggatggtg gctgcggcca ccaacaatct gtgtgaggca      7320
gccaatgcag ctgtacaagg ccatgccagc caggagaagc tcatctcatc agccaagcag      7380
gtagctgcct ccacagccca gctccttgtg gcctgcaagg tcaaggctga ccaggactcg      7440
gaggcaatga aacgacttca ggctgctggc aacgcagtga agcgagcctc agataatctg      7500
gtgaaagcag cacagaaggc tgcagccttt gaagagcagg agaatgagac agtggtggtg      7560
aaagagaaga tggttggcgg cattgcccag atcatcgcag cacaggaaga aatgcttcgg      7620
aaggaacgag agctggaaga ggcgcggaag aaactggccc agatccggca gcagcagtac      7680
aagtttctgc cttcagagct tcgagatgag cactaaagaa gcctcttcta tttaatgcag      7740
acccggccca gagactgtgc gtgccactac caaagccttc tgggctgtcg ggcccaacc       7800 tgcccaaccc cagcactccc caaagtgcct gccaaacccc agggcctggc cccgcccagt      7860
cccgcagtac atcccctgtc ccctccccaa ccccaagtgc cttcatgccc tagggccccc      7920
caagtgcctg cccctcccca gagtattaac gctccaagag tattattaac gctgctgtac      7980
ctcgatctga atctgccggg gccccagccc actccaccct gccagcagct tccagccagt      8040
ccccacagcc tcatcagctc tcttcaccgt tttttgatac tatcttcccc cacccccagc      8100
tacccatagg ggctgcagag ttataagccc caaacaggtc atgctccaat aaaaatgatt      8160
ctacctacaa aaaaaaaaaa aaaaaaa                                         8187

<210> SEQ ID NO 2
<211> LENGTH: 2541
<212> TYPE: PRT
<213> ORGANISM: Homo sapiens

<400> SEQUENCE: 2

Met Val Ala Leu Ser Leu Lys Ile Ser Ile Gly Asn Val Val Lys Thr
1               5                   10                  15

Met Gln Phe Glu Pro Ser Thr Met Val Tyr Asp Ala Cys Arg Ile Ile
                20                  25                  30

Arg Glu Arg Ile Pro Glu Ala Pro Ala Gly Pro Pro Ser Asp Phe Gly
            35                  40                  45

Leu Phe Leu Ser Asp Asp Pro Lys Lys Gly Ile Trp Leu Glu Ala
    50                  55                  60

Gly Lys Ala Leu Asp Tyr Tyr Met Leu Arg Asn Gly Asp Thr Met Glu
65                  70                  75                  80

Tyr Arg Lys Lys Gln Arg Pro Leu Lys Ile Arg Met Leu Asp Gly Thr
                85                  90                  95

Val Lys Thr Ile Met Val Asp Asp Ser Lys Thr Val Thr Asp Met Leu
            100                 105                 110

Met Thr Ile Cys Ala Arg Ile Gly Ile Thr Asn His Asp Glu Tyr Ser
        115                 120                 125

Leu Val Arg Glu Leu Met Glu Glu Lys Lys Glu Glu Ile Thr Gly Thr
    130                 135                 140

Leu Arg Lys Asp Lys Thr Leu Leu Arg Asp Glu Lys Lys Met Glu Lys
145                 150                 155                 160

Leu Lys Gln Lys Leu His Thr Asp Asp Glu Leu Asn Trp Leu Asp His
                165                 170                 175
```

-continued

Gly Arg Thr Leu Arg Glu Gln Gly Val Glu His Glu Thr Leu Leu
            180                 185                 190

Leu Arg Arg Lys Phe Phe Tyr Ser Asp Gln Asn Val Asp Ser Arg Asp
        195                 200                 205

Pro Val Gln Leu Asn Leu Leu Tyr Val Gln Ala Arg Asp Asp Ile Leu
    210                 215                 220

Asn Gly Ser His Pro Val Ser Phe Asp Lys Ala Cys Glu Phe Ala Gly
225                 230                 235                 240

Phe Gln Cys Gln Ile Gln Phe Gly Pro His Asn Glu Gln Lys His Lys
                245                 250                 255

Ala Gly Phe Leu Asp Leu Lys Asp Phe Leu Pro Lys Glu Tyr Val Lys
            260                 265                 270

Gln Lys Gly Glu Arg Lys Ile Phe Gln Ala His Lys Asn Cys Gly Gln
        275                 280                 285

Met Ser Glu Ile Glu Ala Lys Val Arg Tyr Val Lys Leu Ala Arg Ser
    290                 295                 300

Leu Lys Thr Tyr Gly Val Ser Phe Phe Leu Val Lys Glu Lys Met Lys
305                 310                 315                 320

Gly Lys Asn Lys Leu Val Pro Arg Leu Leu Gly Ile Thr Lys Glu Cys
                325                 330                 335

Val Met Arg Val Asp Glu Lys Thr Lys Glu Val Ile Gln Glu Trp Asn
            340                 345                 350

Leu Thr Asn Ile Lys Arg Trp Ala Ala Ser Pro Lys Ser Phe Thr Leu
        355                 360                 365

Asp Phe Gly Asp Tyr Gln Asp Gly Tyr Tyr Ser Val Gln Thr Thr Glu
    370                 375                 380

Gly Glu Gln Ile Ala Gln Leu Ile Ala Gly Tyr Ile Asp Ile Ile Leu
385                 390                 395                 400

Lys Lys Lys Lys Ser Lys Asp His Phe Gly Leu Glu Gly Asp Glu Glu
                405                 410                 415

Ser Thr Met Leu Glu Asp Ser Val Ser Pro Lys Lys Ser Thr Val Leu
            420                 425                 430

Gln Gln Gln Tyr Asn Arg Val Gly Lys Val Glu His Gly Ser Val Ala
        435                 440                 445

Leu Pro Ala Ile Met Arg Ser Gly Ala Ser Gly Pro Glu Asn Phe Gln
    450                 455                 460

Val Gly Ser Met Pro Pro Ala Gln Gln Gln Ile Thr Ser Gly Gln Met
465                 470                 475                 480

His Arg Gly His Met Pro Pro Leu Thr Ser Ala Gln Gln Ala Leu Thr
                485                 490                 495

Gly Thr Ile Asn Ser Ser Met Gln Ala Val Gln Ala Ala Gln Ala Thr
            500                 505                 510

Leu Asp Asp Phe Asp Thr Leu Pro Pro Leu Gly Gln Asp Ala Ala Ser
        515                 520                 525

Lys Ala Trp Arg Lys Asn Lys Met Asp Glu Ser Lys His Glu Ile His
    530                 535                 540

Ser Gln Val Asp Ala Ile Thr Ala Gly Thr Ala Ser Val Val Asn Leu
545                 550                 555                 560

Thr Ala Gly Asp Pro Ala Glu Thr Asp Tyr Thr Ala Val Gly Cys Ala
                565                 570                 575

Val Thr Thr Ile Ser Ser Asn Leu Thr Glu Met Ser Arg Gly Val Lys
            580                 585                 590

Leu Leu Ala Ala Leu Leu Glu Asp Glu Gly Gly Ser Gly Arg Pro Leu

```
                595                 600                 605
Leu Gln Ala Ala Lys Gly Leu Ala Gly Ala Val Ser Glu Leu Leu Arg
            610                 615                 620
Ser Ala Gln Pro Ala Ser Ala Glu Pro Arg Gln Asn Leu Leu Gln Ala
625                 630                 635                 640
Ala Gly Asn Val Gly Gln Ala Ser Gly Glu Leu Leu Gln Gln Ile Gly
            645                 650                 655
Glu Ser Asp Thr Asp Pro His Phe Gln Asp Ala Leu Met Gln Leu Ala
            660                 665                 670
Lys Ala Val Ala Ser Ala Ala Ala Leu Val Leu Lys Ala Lys Ser
            675                 680                 685
Val Ala Gln Arg Thr Glu Asp Ser Gly Leu Gln Thr Gln Val Ile Ala
690                 695                 700
Ala Ala Thr Gln Cys Ala Leu Ser Thr Ser Gln Leu Val Ala Cys Thr
705                 710                 715                 720
Lys Val Val Ala Pro Thr Ile Ser Ser Pro Val Cys Gln Glu Gln Leu
            725                 730                 735
Val Glu Ala Gly Arg Leu Val Ala Lys Ala Val Glu Gly Cys Val Ser
            740                 745                 750
Ala Ser Gln Ala Ala Thr Glu Asp Gly Gln Leu Leu Arg Gly Val Gly
            755                 760                 765
Ala Ala Ala Thr Ala Val Thr Gln Ala Leu Asn Glu Leu Leu Gln His
            770                 775                 780
Val Lys Ala His Ala Thr Gly Ala Gly Pro Ala Gly Arg Tyr Asp Gln
785                 790                 795                 800
Ala Thr Asp Thr Ile Leu Thr Val Thr Glu Asn Ile Phe Ser Ser Met
                805                 810                 815
Gly Asp Ala Gly Glu Met Val Gly Gln Ala Arg Ile Leu Ala Gln Ala
            820                 825                 830
Thr Ser Asp Leu Val Asn Ala Ile Lys Ala Asp Ala Glu Gly Glu Ser
            835                 840                 845
Asp Leu Glu Asn Ser Arg Lys Leu Leu Ser Ala Ala Lys Ile Leu Ala
850                 855                 860
Asp Ala Thr Ala Lys Met Val Glu Ala Ala Lys Gly Ala Ala Ala His
865                 870                 875                 880
Pro Asp Ser Glu Glu Gln Gln Gln Arg Leu Arg Glu Ala Ala Glu Gly
                885                 890                 895
Leu Arg Met Ala Thr Asn Ala Ala Ala Gln Asn Ala Ile Lys Lys Lys
            900                 905                 910
Leu Val Gln Arg Leu Glu His Ala Ala Lys Gln Ala Ala Ala Ser Ala
            915                 920                 925
Thr Gln Thr Ile Ala Ala Ala Gln His Ala Ala Ser Thr Pro Lys Ala
            930                 935                 940
Ser Ala Gly Pro Gln Pro Leu Leu Val Gln Ser Cys Lys Ala Val Ala
945                 950                 955                 960
Glu Gln Ile Pro Leu Leu Val Gln Gly Val Arg Gly Ser Gln Ala Gln
                965                 970                 975
Pro Asp Ser Pro Ser Ala Gln Leu Ala Leu Ile Ala Ala Ser Gln Ser
            980                 985                 990
Phe Leu Gln Pro Gly Gly Lys Met Val Ala Ala Lys Ala Ser Val
            995                 1000                1005
Pro Thr Ile Gln Asp Gln Ala Ser Ala Met Gln Leu Ser Gln Cys Ala
            1010                1015                1020
```

-continued

Lys Asn Leu Gly Thr Ala Leu Ala Glu Leu Arg Thr Ala Ala Gln Lys
1025                1030                1035                1040

Ala Gln Glu Ala Cys Gly Pro Leu Glu Met Asp Ser Ala Leu Ser Val
                1045                1050                1055

Val Gln Asn Leu Glu Lys Asp Leu Gln Glu Val Lys Ala Ala Ala Arg
    1060                1065                1070

Asp Gly Lys Leu Lys Pro Leu Pro Gly Glu Thr Met Glu Lys Cys Thr
        1075                1080                1085

Gln Asp Leu Gly Asn Ser Thr Lys Ala Val Ser Ser Ala Ile Ala Gln
    1090                1095                1100

Leu Leu Gly Glu Val Ala Gln Gly Asn Glu Asn Tyr Ala Gly Ile Ala
1105                1110                1115                1120

Ala Arg Asp Val Ala Gly Gly Leu Arg Ser Leu Ala Gln Ala Ala Arg
                1125                1130                1135

Gly Val Ala Ala Leu Thr Ser Asp Pro Ala Val Gln Ala Ile Val Leu
            1140                1145                1150

Asp Thr Ala Ser Asp Val Leu Asp Lys Ala Ser Ser Leu Ile Glu Glu
        1155                1160                1165

Ala Lys Lys Ala Ala Gly His Pro Gly Asp Pro Glu Ser Gln Gln Arg
    1170                1175                1180

Leu Ala Gln Val Ala Lys Ala Val Thr Gln Ala Leu Asn Arg Cys Val
1185                1190                1195                1200

Ser Cys Leu Pro Gly Gln Arg Asp Val Asp Asn Ala Leu Arg Ala Val
                1205                1210                1215

Gly Asp Ala Ser Lys Arg Leu Leu Ser Asp Ser Leu Pro Pro Ser Thr
            1220                1225                1230

Gly Thr Phe Gln Glu Ala Gln Ser Arg Leu Asn Glu Ala Ala Ala Gly
        1235                1240                1245

Leu Asn Gln Ala Ala Thr Glu Leu Val Gln Ala Ser Arg Gly Thr Pro
    1250                1255                1260

Gln Asp Leu Ala Arg Ala Ser Gly Arg Phe Gly Gln Asp Phe Ser Thr
1265                1270                1275                1280

Phe Leu Glu Ala Gly Val Glu Met Ala Gly Gln Ala Pro Ser Gln Glu
                1285                1290                1295

Asp Arg Ala Gln Val Val Ser Asn Leu Lys Gly Ile Ser Met Ser Ser
            1300                1305                1310

Ser Lys Leu Leu Leu Ala Ala Lys Ala Leu Ser Thr Asp Pro Ala Ala
        1315                1320                1325

Pro Asn Leu Lys Ser Gln Leu Ala Ala Ala Ala Arg Ala Val Thr Asp
    1330                1335                1340

Ser Ile Asn Gln Leu Ile Thr Met Cys Thr Gln Gln Ala Pro Gly Gln
1345                1350                1355                1360

Lys Glu Cys Asp Asn Ala Leu Arg Glu Leu Glu Thr Val Arg Glu Leu
                1365                1370                1375

Leu Glu Asn Pro Val Gln Pro Ile Asn Asp Met Ser Tyr Phe Gly Cys
            1380                1385                1390

Leu Asp Ser Val Met Glu Asn Ser Lys Val Leu Gly Glu Ala Met Thr
        1395                1400                1405

Gly Ile Ser Gln Asn Ala Lys Asn Gly Asn Leu Pro Glu Phe Gly Asp
    1410                1415                1420

Ala Ile Ser Thr Ala Ser Lys Ala Leu Cys Gly Phe Thr Glu Ala Ala
1425                1430                1435                1440

-continued

```
Ala Gln Ala Ala Tyr Leu Val Gly Val Ser Asp Pro Asn Ser Gln Ala
            1445                1450                1455

Gly Gln Gln Gly Leu Val Glu Pro Thr Gln Phe Ala Arg Ala Asn Gln
        1460                1465                1470

Ala Ile Gln Met Ala Cys Gln Ser Leu Gly Glu Pro Gly Cys Thr Gln
        1475                1480                1485

Ala Gln Val Leu Ser Ala Thr Ile Val Ala Lys His Thr Ser Ala
        1490                1495                1500

Leu Cys Asn Ser Cys Arg Leu Ala Ser Ala Arg Thr Thr Asn Pro Thr
1505                1510                1515                1520

Ala Lys Arg Gln Phe Val Gln Ser Ala Lys Glu Val Ala Asn Ser Thr
            1525                1530                1535

Ala Asn Leu Val Lys Thr Ile Lys Ala Leu Asp Gly Ala Phe Thr Glu
            1540                1545                1550

Glu Asn Arg Ala Gln Cys Arg Ala Ala Thr Ala Pro Leu Leu Glu Ala
            1555                1560                1565

Val Asp Asn Leu Ser Ala Phe Ala Ser Asn Pro Glu Phe Ser Ser Ile
    1570                1575                1580

Pro Ala Gln Ile Ser Pro Glu Gly Arg Ala Ala Met Glu Pro Ile Val
1585                1590                1595                1600

Ile Ser Ala Lys Thr Met Leu Glu Ser Ala Gly Gly Leu Ile Gln Thr
            1605                1610                1615

Ala Arg Ala Leu Ala Val Asn Pro Arg Asp Pro Pro Ser Trp Ser Val
            1620                1625                1630

Leu Ala Gly His Ser Arg Thr Val Ser Asp Ser Ile Lys Lys Leu Ile
            1635                1640                1645

Thr Ser Met Arg Asp Lys Ala Pro Gly Gln Leu Glu Cys Glu Thr Ala
    1650                1655                1660

Ile Ala Ala Leu Asn Ser Cys Leu Arg Asp Leu Asp Gln Ala Ser Leu
1665                1670                1675                1680

Ala Ala Val Ser Gln Gln Leu Ala Pro Arg Glu Gly Ile Ser Gln Glu
            1685                1690                1695

Ala Leu His Thr Gln Met Leu Thr Ala Val Gln Glu Ile Ser His Leu
            1700                1705                1710

Ile Glu Pro Leu Ala Asn Ala Ala Arg Ala Glu Ala Ser Gln Leu Gly
    1715                1720                1725

His Lys Val Ser Gln Met Ala Gln Tyr Phe Glu Pro Leu Thr Leu Ala
            1730                1735                1740

Ala Val Gly Ala Ala Ser Lys Thr Leu Ser His Pro Gln Gln Met Ala
1745                1750                1755                1760

Leu Leu Asp Gln Thr Lys Thr Leu Ala Glu Ser Ala Leu Gln Leu Leu
            1765                1770                1775

Tyr Thr Ala Lys Glu Ala Gly Gly Asn Pro Lys Gln Ala Ala His Thr
    1780                1785                1790

Gln Glu Ala Leu Glu Glu Ala Val Gln Met Met Thr Glu Ala Val Glu
        1795                1800                1805

Asp Leu Thr Thr Thr Leu Asn Glu Ala Ala Ser Ala Ala Gly Val Val
    1810                1815                1820

Gly Gly Met Val Asp Ser Ile Thr Gln Ala Ile Asn Gln Leu Asp Glu
1825                1830                1835                1840

Gly Pro Met Gly Glu Pro Glu Gly Ser Phe Val Asp Tyr Gln Thr Thr
            1845                1850                1855

Met Val Arg Thr Ala Lys Ala Ile Ala Val Thr Val Gln Glu Met Val
```

-continued

```
            1860                1865                1870
Thr Lys Ser Asn Thr Ser Pro Glu Glu Leu Gly Pro Leu Ala Asn Gln
        1875                1880                1885
Leu Thr Ser Asp Tyr Gly Arg Leu Ala Ser Glu Ala Lys Pro Ala Ala
        1890                1895                1900
Val Ala Ala Glu Asn Glu Glu Ile Gly Ser His Ile Lys His Arg Val
1905                1910                1915                1920
Gln Glu Leu Gly His Gly Cys Ala Ala Leu Val Thr Lys Ala Gly Ala
                1925                1930                1935
Leu Gln Cys Ser Pro Ser Asp Ala Tyr Thr Lys Lys Glu Leu Ile Glu
                1940                1945                1950
Cys Ala Arg Arg Val Ser Glu Lys Val Ser His Val Leu Ala Ala Leu
        1955                1960                1965
Gln Ala Gly Asn Arg Gly Thr Gln Ala Cys Ile Thr Ala Ala Ser Ala
        1970                1975                1980
Val Ser Gly Ile Ile Ala Asp Leu Asp Thr Thr Ile Met Phe Ala Thr
1985                1990                1995                2000
Ala Gly Thr Leu Asn Arg Glu Gly Thr Glu Thr Phe Ala Asp His Arg
                2005                2010                2015
Glu Gly Ile Leu Lys Thr Ala Lys Val Leu Val Glu Asp Thr Lys Val
                2020                2025                2030
Leu Val Gln Asn Ala Ala Gly Ser Gln Glu Lys Leu Ala Gln Ala Ala
            2035                2040                2045
Gln Ser Ser Val Ala Thr Ile Thr Arg Leu Ala Asp Val Val Lys Leu
        2050                2055                2060
Gly Ala Ala Ser Leu Gly Ala Glu Asp Pro Glu Thr Gln Val Val Leu
2065                2070                2075                2080
Ile Asn Ala Val Lys Asp Val Ala Lys Ala Leu Gly Asp Leu Ile Ser
                2085                2090                2095
Ala Thr Lys Ala Ala Ala Gly Lys Val Gly Asp Asp Pro Ala Val Trp
            2100                2105                2110
Gln Leu Lys Asn Ser Ala Lys Val Met Val Thr Asn Val Thr Ser Leu
        2115                2120                2125
Leu Lys Thr Val Lys Ala Val Glu Asp Glu Ala Thr Lys Gly Thr Arg
        2130                2135                2140
Ala Leu Glu Ala Thr Thr Glu His Ile Arg Gln Glu Leu Ala Val Phe
2145                2150                2155                2160
Cys Ser Pro Glu Pro Pro Ala Lys Thr Ser Thr Pro Glu Asp Phe Ile
            2165                2170                2175
Arg Met Thr Lys Gly Ile Thr Met Ala Thr Ala Lys Ala Val Ala Ala
        2180                2185                2190
Gly Asn Ser Cys Arg Gln Glu Asp Val Ile Ala Thr Ala Asn Leu Ser
        2195                2200                2205
Arg Arg Ala Ile Ala Asp Met Leu Arg Ala Cys Lys Glu Ala Ala Tyr
        2210                2215                2220
His Pro Glu Val Ala Pro Asp Val Arg Leu Arg Ala Leu His Tyr Gly
2225                2230                2235                2240
Arg Glu Cys Ala Asn Gly Tyr Leu Glu Leu Leu Asp His Val Leu Leu
            2245                2250                2255
Thr Leu Gln Lys Pro Ser Pro Glu Leu Lys Gln Gln Leu Thr Gly His
            2260                2265                2270
Ser Lys Arg Val Ala Gly Ser Val Thr Glu Leu Ile Gln Ala Ala Glu
        2275                2280                2285
```

```
Ala Met Lys Gly Thr Glu Trp Val Asp Pro Glu Asp Pro Thr Val Ile
    2290                2295                2300

Ala Glu Asn Glu Leu Leu Gly Ala Ala Ala Ile Glu Ala Ala Ala
2305                2310                2315                2320

Lys Lys Leu Glu Gln Leu Lys Pro Arg Ala Lys Pro Lys Glu Ala Asp
                2325                2330                2335

Glu Ser Leu Asn Phe Glu Glu Gln Ile Leu Glu Ala Ala Lys Ser Ile
            2340                2345                2350

Ala Ala Ala Thr Ser Ala Leu Val Lys Ala Ala Ser Ala Ala Gln Arg
        2355                2360                2365

Glu Leu Val Ala Gln Gly Lys Val Gly Ala Ile Pro Ala Asn Ala Leu
    2370                2375                2380

Asp Asp Gly Gln Trp Ser Gln Gly Leu Ile Ser Ala Ala Arg Met Val
2385                2390                2395                2400

Ala Ala Ala Thr Asn Asn Leu Cys Glu Ala Ala Asn Ala Ala Val Gln
                2405                2410                2415

Gly His Ala Ser Gln Glu Lys Leu Ile Ser Ser Ala Lys Gln Val Ala
            2420                2425                2430

Ala Ser Thr Ala Gln Leu Leu Val Ala Cys Lys Val Lys Ala Asp Gln
        2435                2440                2445

Asp Ser Glu Ala Met Lys Arg Leu Gln Ala Ala Gly Asn Ala Val Lys
    2450                2455                2460

Arg Ala Ser Asp Asn Leu Val Lys Ala Ala Gln Lys Ala Ala Ala Phe
2465                2470                2475                2480

Glu Glu Gln Glu Asn Glu Thr Val Val Val Lys Glu Lys Met Val Gly
                2485                2490                2495

Gly Ile Ala Gln Ile Ile Ala Ala Gln Glu Glu Met Leu Arg Lys Glu
            2500                2505                2510

Arg Glu Leu Glu Glu Ala Arg Lys Lys Leu Ala Gln Ile Arg Gln Gln
        2515                2520                2525

Gln Tyr Lys Phe Leu Pro Ser Glu Leu Arg Asp Glu His
    2530                2535                2540

<210> SEQ ID NO 3
<211> LENGTH: 11650
<212> TYPE: DNA
<213> ORGANISM: Homo sapiens

<400> SEQUENCE: 3
atggtggccc tgtccttaaa gatttgtgtg cgccactgca acgtggtgaa gaccatgcag      60
tttgaaccat ctacagctgt gtacgatgcg tgtcgagtca ttcgggaacg ggtgcctgag     120
gcacaaactg ggcaagcttc tgactatgga ctctttcttt cggatgaaga cccgaggaaa     180
gggatttggc tggaagcggg cagaacactg gattactaca tgttgcggaa tgggatatt     240 ttggaatata aaagaaaca gagacctcag aaaatccgga tgctggatgg atctgtgaag     300
acagtgatgg tggatgattc caagactgtg ggggagctcc tggtcactat ttgtagcaga     360
ataggaataa caattatga agaatactcc ttaatccaag aaactattga agaaagaaaa     420
gaggaaggaa cgggcacact caaaaaagac aggacactgt acagagatga ggaaaatg     480 gagaagttga aggccaagct gcacacagat gatgacctaa attggctgga tcacagccga     540
acattcagag aacaaggagt agatgaaaac gaaacgttgc tgcttagacg gaagttcttt     600
tactctgatc agaatgtaga ttcgagagac cccgtgcagc tgaacttgct ttatgttcag     660
```

```
gcacgggatg acatcctgaa tggctctcac cctgtctcct tcgagaaagc ttgtgagttt    720
ggtggatttc aagcccagat acaatttgga cctcatgtgg aacataaaca caaacctgga    780
tttttagatc tgaaggaatt cctgcccaaa gaatatatca agcagagagg agctgaaaag    840
aggatctttc aggagcataa gaactgcgga gagatgagtg agatagaagc caaggtcaag    900
tacgtcaaac tcgcacggtc cctccgcaca tatggcgtgt ccttcttcct ggtgaaggag    960
aagatgaaag gcaagaacaa gctggtgcct cgcctgctgg ggatcaccaa agactcggtg   1020
atgcgcgtgg atgagaagac caaggaagtg ctgcaggagt ggcccctcac caccgtcaag   1080
cgctgggcag cctcacccaa gagcttcaca ctggattttg gggagtatca ggaaagctac   1140
tattcagtac aaaccaccga gggagagcag atatcccagc tgattgcagg ctacattgac   1200
atcatcctga aaagaaaaca agtaaagat cgatttggac tagaaggtga tgaggagtca   1260
accatgttag aagagtccgt ttccccaaaa aagtccacca tcttgcagca gcagttcaac   1320
cggaccggga aggcagagca cggctcagtg gcgctgccgg ccgtgatgcg ctcgggctcc   1380
agcgggcctg agaccttcaa cgttggcagc atgccctcgc acagcagca ggtcatggtt   1440 gggcagatgc accgaggcca catgccgcca ctgacctcag cccagcaggc cctgatgggg   1500
accatcaaca caagcatgca cgccgtccag caggcccagg atgatctcag tgagctcgac   1560
tcgctgccac ctctcggcca ggatatggca tctagggtat gggttcagaa caaagtcgac   1620
gaatccaaac acgaaatcca ttctcaagtt gatgctatca cggccggaac ggcttcagtt   1680
gttaacctca cagctggtga ccctgcagac actgactaca cagctgtggg atgtgcgatc   1740
accactattt cttccaacct gacggagatg tccaagggtg tgaagctatt ggccgccctc   1800
atggatgatg aggtgggcag cggggaggac ttgctcagag ctgccaggac cctcgctggg   1860
gcggtgtcag acttgctgaa agctgtgcag cctacttctg gagagcctcg acagacagtt   1920
ttgactgctg ctggcagcat cggacaagcc agtggggatc ttctgagaca gattggagag   1980
aatgagactg atgagcgatt ccaggatgtt ttaatgagtt tggccaaagc tgttgccaat   2040
gcagctgcca tgttggtact aaaggcaaag aatgttgccc aagtggccga agacactgtc   2100
ctacagaaca gggtaattgc tgctgccacc cagtgtgccc tctccacctc ccagcttgtg   2160
gcatgtgcca aggttgtgag ccccactatt agctcccctg tgtgccagga gcagctgatt   2220
gaagcaggga gctggtgga ccgctcggtg gagaactgtg tccgtgcctg ccaggcggcc   2280
actaccgata gtgagctcct gaagcaggtc agcgcagcgg ccagcgtggt cagccaggcc   2340
ctccatgatc tcctgcagca tgtgcggcag tttgccagcc gaggcgagcc catcggccgc   2400
tacgaccagg ctactgacac catcatgtgt gtcaccgaga gcatcttcag ctccatgggt   2460
gacgctggtg aaatggtgcg ccaggcgcgg gttctggccc aagccacatc agacctcgtc   2520
aatgccatga ggtcagatgc agaagccgaa atcgacatgg agaattcaaa gaagctcctg   2580
gcagcagcaa aactcttagc tgactccact gctcgcatgg tggaagctgc aaagggggct   2640
gcagccaacc cagagaatga ggaccagcag caaaggctga gagaagctgc agaaggcctc   2700
cgggtagcaa ccaacgcagc tgcccagaat gctattaaga aaaaaattgt caaccgactg   2760
gaggttgcag ccaagcaggc cgcagcggca gccacacaga ccatcgccgc ctcccagaat   2820
gcagctgttt ccaacaagaa ccctgcggcc cagcagcagc tggtccagag ttgcaaggca   2880
gtggctgatc acatccctca gctggtccag ggagtgaggg ggagccaagc tcaagctgaa   2940
gacctgagtg cccagctggc tctcatcatc tccagccaga acttcctcca gcctggaagc   3000
aagatggtgt cctctgccaa agccgcagtg cccaccgtga gtgaccaggc cgcagccatg   3060
```

```
cagctgagcc agtgtgccaa gaacctggcc accagcttgg cggagctgcg taccgcctcg    3120
cagaaggccc atgaagcttg tggtccgatg gaaatcgatt cagctctgaa tacggtgcag    3180
acgcttaaga atgaactgca ggatgccaag atggcagccg tggagagcca gctgaagcca    3240
cttccagggg aaacgctgga aaaatgtgct caggacctgg gaagcacatc caaggcggtg    3300
ggctcctcca tggcacagct gctgacctgt gctgctcaag caacgaaca ctacacaggg     3360 gtggctgcta gagagacggc ccaagctctg aaaacactgg cccaggccgc cgtggagtg    3420 gctgcatcga caaccgaccc cgcggccgcc catgccatgt tagattctgc tcgagacgtg    3480
atggagggct ccgccatgct cattcaagag gccaagcagg ccctgattgc acctggagat    3540
gcagagcgtc aacaaagact ggctcaggtg gctaaagccg tctcacactc cttgaataac    3600
tgcgtaaatt gcctccctgg gcagaaggat gtggacgtgg ccttgaagag catcggggag    3660
tccagcaaga agctgcttgt ggattcgcta cctccaagca cgaagccttt ccaggaagcc    3720
cagagtgaac tgaaccaggc agcagctgat ctgaaccagt ctgctgggga agtggtccat    3780
gccacccggg gccagagtgg agagttggct gcagcctctg gaaagttcag tgatgatttt    3840
gatgaattcc tcgatgctgg cattgagatg gctggccaag ctcagacaaa agaagaccag    3900
atccaagtga tagggaacct caagaatatc tcgatggcat ccagcaagct gctgttagct    3960
gccaagtctc tctctgtaga tccaggagct cccaatgcga aaatctcct ggctgcagct    4020 gcaagagctg tgacagagag catcaatcaa ctcatcactc tgtgtaccca acaagctccg    4080
ggccagaaag agtgcgataa tgccctgcgg gagctcgaga ctgtgaaggg gatgttggac    4140
aatcctaatg aacctgttag tgacctctct tactttgact gcattgagag tgtgatggaa    4200
aactccaagg ttctgggtga atcgatggca gggatttcac agaatgccaa gaccggagac    4260
ctccctgcct ttggggaatg tgtggggatt gcatccaagg ctctctgtgg gctgacagag    4320
gctgcagccc aggctgcata cttggttggc atctctgatc caaacagcca ggcaggccac    4380
cagggcctgg tggaccccat ccagtttgcc agggctaacc aggccatcca gatggcatgc    4440
cagaacttgg tggaccctgg cagcagccca tcacaggtcc tgtcagccgc acaattgtt    4500 gccaagcaca cgtcagcctt gtgcaatgcc tgccgcatcg cctcatccaa gacggccaac    4560
ccagtagcca agaggcactt cgtccagtca gccaaggaag tcgccaacag cactgccaac    4620
ctggtgaaga ccatcaaggc cctggatggg gatttctctg aagacaaccg caataagtgt    4680
cgcatcgcca ccgcaccctt gattgaagct gtggagaacc tgacagcgtt cgcctcaaac    4740
cctgagtttg tcagcattcc tgcccagatc agctccgagg gttcccaggc acaggaacca    4800
atcctggtct cagccaagac catgctggag agttcatcgt acctcattcg cactgcacgc    4860
tctctggcca tcaaccccaa agacccaccc acctggtctg tactggctgg acattcccat    4920
acagtgtccg actccatcaa gagtctcatc acttctatca gggacaaggc ccctggacag    4980
agggagtgtg attactccat cgatggcatc aaccggtgca tccgggacat cgagcaggcc    5040
tcgctggccg ccgtcagcca gagcctggcc acgagggacg acatctctgt ggaggccctg    5100
caggagcagc tgacttcggt ggtccaggaa atcggacacc ttatcgatcc catcgccaca    5160
gcggctcggg gagaagcagc tcagctggga cataaggtga cacaactggc aagctatttt    5220
gagcccttga tcttagccgc agttggtgtg gcctccaaga ttcttgatca tcagcagcag    5280
atgacggtgc tggaccagac caagactctc gcagagtctg ccttgcagat gttgtatgca    5340
gccaaagaag gtggcggaaa ccccaaggca caacacaccc atgacgccat cacagaggcc    5400
```

-continued

```
gcccagttga tgaaggaagc cgtggatgac atcatggtga cgctgaacga agctgccagt    5460
gaagtggggc tggttggggg catggtggac gccattgcag aagccatgag caagctggat    5520
gaaggcactc ctccagaacc aaagggaaca tttgtcgact atcagacgac tgtggttaaa    5580
tactccaaag ccattgcggt gacagctcag gaaatgatga ctaagtcggt tactaacccg    5640
gaggagttgg gaggactggc ttcacaaatg accagtgact atgggcacct ggctttccag    5700
ggccagatgg cagcagccac ggcggaacca gaggagatcg gattccagat tcgcactcgt    5760
gtgcaggacc tgggccacgg ctgtatcttc ctggtgcaga aggcaggggc cctccaggtc    5820
tgccccacag acagctacac caagagggag ctgatcgaat cgcccgtgc cgtcacggaa     5880
aaggtctcct tggtgctctc ggctctccag gccgggaaca aaggaaccca ggcatgcatt    5940
acagccgcca ccgctgtgtc tgggatcatt gccgacctgg acaccaccat tatgtttgca    6000
acagcgggga cgctgaatgc agagaacagt gagaccttcg cagaccacag ggagaacatt    6060
ctcaagacgg ccaaggcctt ggtagaagac acgaaactac ttgtgtcagg agctgcgtcc    6120
actcctgaca agctggccca gcggcccag tcctcagcag ccaccatcac ccagctcgca     6180
gaagtggtca gctgggggc agccagcctg ggctccgacg accccgagac ccaggtggtt     6240
ttgatcaatg ccatcaaaga tgtggccaag ccccttctg atctcatcag tgctaccaag      6300
ggagctgcca gcaagccagt ggacgaccct tccatgtacc agctcaaggg ggctgccaag    6360
gtgatggtga ccaatgtcac ctcgctcctc aagactgtaa aggcagtgga ggatgaggcc    6420
acccggggca ccagggcgct tgaggccaca attgaatgca taaagcagga gcttacggtg    6480
ttccagtcaa aagacgtacc tgaaaagaca tcatcacctg aagaatccat aaggatgacg    6540
aaaggcatca ccatggcaac agccaaagcc gtggcagctg ggaactcatg tagacaggag    6600
gacgtgattg ctactgccaa cctgagccgg aaagccgtgt cagatatgtt gacggcttgc    6660
aagcaagcat ccttccaccc cgatgtcagt gacgaggtga gaaccagagc cttgcgtttc    6720
gggacggagt gcacccttgg ctacttggac ctcctggagc acgtcttggt gattcttcag    6780
aaaccaaccc cagaattcaa gcagcagctg gccgctttct ccaagcgagt cgccggcgct    6840
gtgacagagc tcatccaggc ggcggaagcc atgaaaggaa cagagtgggt ggatccagaa    6900
gacccaactg tcattgcaga aacagagtta ctgggggctg cagcatccat cgaagctgct    6960
gctaagaagt tagagcaact gaagccaaga gcaaaaccaa acaagcgga tgagaccctg     7020
gactttgagg aacagatctt ggaagctgct aaatccattg ctgctgccac aagcgccctg    7080
gtcaaatcgg cctcagcagc ccagaggag ctggtggccc aaggaaaggt gggctccatc     7140
cctgccaatg ctgcagacga cggacagtgg tcacagggc tgatttctgc tgcccggatg     7200
gtggcggctc cgaccagcag tctctgtgag gcggccaatg cctccgttca gggacacgcc    7260
agcgaggaga agctcatctc atctgccaag caggtcgccg cttccacggc tcagctgctg    7320
gtggcctgca aggtgaaggc cgaccaggat tcagaggcca tgaggcggct acaggcggca    7380
ggaaatgctg tgaaaagagc ctcagacaat cttgtccgtg cagcccagaa ggcagctttt    7440
ggcaaagctg atgacgacga tgttgtagtg aaaaccaagt ttgtggggg cattgctcag    7500
atcatcgccg cccaggaaga aatgctaaag aaagagcgag aactggaaga agcaaggaaa    7560
aaactggccc aaatccgcca gcagcagtat aagttttac ccaccgagct gagggaagat     7620
gagggctaaa ggtgcgagcc cagatggcga gccccagggg atggccctgg ctgaactgga    7680
cagacagtgt tcctgagagg ctgggcactt agctggaaac cgcccacctc cctcccgggt    7740
gagcctggag ccctgcgtgc ttgttctcac atctctgtcc cgtcggcact ggctgcatga    7800
```

```
tcgtgatgtc acacggtaca atgtcctacc cacaactcct ctgccgcctc ccctcatgcc    7860
tcaccgtgtc tcaggagaga ggggtgcacg tttcatggac tgttaccaac aaagaaaagt    7920
cagtattatg ttgttctcag acactttggc ttttgttggt ccttctctta ggcctgctcc    7980
tggacctctt tatgatattg tgataggaa aaaatcatt gacgtcatag aatattcttc      8040
ttcctctcag gagaagacgg aagctggagt tggacatggt tcataaaagc cagaaacaca    8100
aacccgtgtg gactccggga gggtgactca ggtcctcctt ccatgtcttg agcactggct    8160
cacccagggg gtgaaaaatt cccgcccctg tttgcacgct tcttgcctc cgtgtgtaag     8220
ctccttgtac aacccagacc catcttgtat tttgtggccc agaaaactga acgattattt    8280
tgttcctccg tagtccaaag ggcagagttg cggaaggccg tcgggcttg gtgagcaggg     8340
gctgtaatac agtctgtggg ctccttaccc tgcagaggct gtttcagctc acacagagtc    8400
atccacacaa acccacggct cccagttgac agtcagtgga atgctcgtct ccttagcgtc    8460
cagggtgggg attctgctgg aataaagagc ttcctcagtg actcatcttt aggtcccacg    8520
ctggtttctg tgccttcaga atggtcacaa gcccggattg gaaggatct gcttacaaac     8580
ctgtcccctg tcctccaacc caaaacgcct ttttttctgt cttaatatcc agaaaatcta    8640
aatgcatcct aaaatcaatg tgaaccttta acaagatagt tttacttatt atcacataag    8700
acataagatg ttttcatttt ctggatgtca cacttccaga atttcatatt tttcccctct    8760
tttctttccc cttttcagag ccctcccata ggaagggaag ggcttgaatt taccttaat     8820
ctgcaccttt agccaaggca gtgcatgaa gatgaatggc tcgtgggaca gaatctaatg     8880
ccagggagca ggagtgtttg aaagaattca tagtggggaa ggtaaaagtt aatggaagta    8940
catgattttc aaaactggta acagttaaag gcactcaccc tccgcctctc tctctctctc    9000
tctctctggt gtgctatcat gtcttggact ccatccacac tatagtttca aagttccact    9060
gacgggggaa agttggtgct ttggtcctcc gaagatgtca cctttcgacc ttgcccgatc    9120
ttgtttcacc agactctagc ccatgtcatg gtttttaaaat acataaactt ctgacagctt    9180
cccatatttta taagttactt ataagtgctg cacgtattag aattttttttt tttcagacca    9240
gtaaagttag agaaaagacg ctgtaaagga aagcaagtg agagtatgtg taggacactg    9300
acagtgtgtg ggcaccagtt ctgaagagga ggggagctgc tggagcccta gctgttggg    9360
gaaaagctgg cacactcttg gctcgccctc tttgagtgga gctgatccaa cacctcatgc    9420
ctgccttggc cggacactga gaggaggggc acacgtgctt ccagagacac tcaggagtca    9480
gaccccaatg ctcagagtca caatgtgttc atggcctcct gtaacaggac tctgggatc     9540
ccctctgtgg cccagcccac cccaccctct gctcttctat gctgtgccca gggcagctgc    9600
cctcttctgc ctgtgcccca tcccatcctg aaaacccagg accaaggcag gggcaggcag    9660
ccagttcttc caccttgcct cagagtcatt taaaaccttt actgcatttg ataccagaaa    9720
agcctccaga gacaaaccaa atgcaaaggc ctttccttta taactctaaa gaacaggcat    9780
cgaaagttta tttttgtagg agctatataa atactcacct ttctggagtc gtccagtgct    9840
gggagctttg gggagtttgg ttctcagtta tcacctggta tggtcccagt ttctcatctg    9900
tcctttcctc atccaccctg cacatgtgta tgtgaacggc ttcgtggccg gtgtggtggt    9960
ttctcatttc ataagatagt tgaagggcca tgccttgtct ggatgttatt taataggcac    10020
tactgcggtg tcctcagatg gtactgaggg ggccttctgg tccttcaaag gaaaataaca    10080
caggcatgag ttcatttggg agtgtgaact ttcagaacac ctaataagag agtggtgtca    10140
```

-continued

```
gagtaaaaac ggccccaggt ctggagcata gaagtgtatc tctgtgaaga gagagccggt    10200
gtgttgacat gtggttcttc tcacacccct ctactcctcg agggctttga atccttgggc    10260
tgattttgt gccagaaatt gctgttcccg atggccaaaa ggggaacctg aactggattt     10320
cagaactgcc cagtgatttg aaaatttaga ttttacttgg gcctttcagg agtctttaga   10380
tagggatgct gaggtcatat ttagttcaat gaacagccct tgtttaagtt ttgccagtgt    10440
ccagccagct gtggccctgg ccatctgtgc aggcaggttc ctcaattcct ggttggccct    10500
gcagtcggtc aacacagtcc ctccaggtcg gctgcagagg cagctgccca gcctgcagtc    10560
tatgcacggg ccttaagaaa tgagctgcct gtagcctcac ggcatatgct tttatcaggg    10620
aaaacccttc gagcttcttc tgattctcac ctgcttgctt tctggctgtc ttagtcagtg    10680
tgtttacagg caactaaagc ctgttcctaa tttatcaaaa aattataacc aaaattcacc    10740
atagcctaag agagtaaacc ccacctccaa agtgatgcca aggccaaaac ctcatcaagg    10800
aaccagacac aggtcaaaag tggtgagcaa gccatggtct ctgctcctgg ggaactcaca    10860
cgctgacccc cgaggagcct tggtttcctc cctggcagat agtccccaga atcttctctc    10920
ccagctttga ggttctgggc tctggaaagg cctctgggat gctggcctta agatctcagc    10980
acagactatc agcatgttcc attctcagat tcctggagga aaggtaccct ctgttgacca    11040
aggggctggc tgcttctgag acttaccaac ccaagaaatt tggagacatt cccctcaggc    11100
taaaaggcag cggtccccag agttcagaaa gcaaagatc ttgacaactg tgccagtagt     11160
ggctctggtc ctatctctcc acagtgctgg cctctgctgg ggaaggcatc tttcccaaag    11220
gtatccccaa gtaccatgtt gaaaatgtcc tcagtctgtt gctccatctt tctgagcctc    11280
tgcttggtat gtcatgttta tggtcactac ggatgagtgt gtgcagagtt tgggttgatt    11340
cttttaaatg ctacaaacaa gagctatttc ttttcaataa aaaaggtttg gattcggcct    11400
cttcctctga gcccacctcc cagccctcca gggagcatca gtgtacctga gtcactttgt    11460
ctgcatctct tcatcccaca aaacacgagg ctgggtctca ttcagcggcc tctcaccaac    11520
cttcaagatc cagaagaaaa caggaacgtt cagctctgcc ctgtgtcgta tctaatcaca    11580
tacattaatt tatctaacca cataagttat tttttttat ttgccagaaa taaaccttta     11640
aaggaacaaa                                                           11650
```

<210> SEQ ID NO 4
<211> LENGTH: 2542
<212> TYPE: PRT
<213> ORGANISM: Homo sapiens

<400> SEQUENCE: 4

```
Met Val Ala Leu Ser Leu Lys Ile Cys Val Arg His Cys Asn Val Val
1               5                   10                  15

Lys Thr Met Gln Phe Glu Pro Ser Thr Ala Val Tyr Asp Ala Cys Arg
            20                  25                  30

Val Ile Arg Glu Arg Val Pro Glu Ala Gln Thr Gly Gln Ala Ser Asp
        35                  40                  45

Tyr Gly Leu Phe Leu Ser Asp Glu Asp Pro Arg Lys Gly Ile Trp Leu
    50                  55                  60

Glu Ala Gly Arg Thr Leu Asp Tyr Tyr Met Leu Arg Asn Gly Asp Ile
65                  70                  75                  80

Leu Glu Tyr Lys Lys Lys Gln Arg Pro Gln Lys Ile Arg Met Leu Asp
                85                  90                  95

Gly Ser Val Lys Thr Val Met Val Asp Asp Ser Lys Thr Val Gly Glu
```

```
            100                 105                 110
Leu Leu Val Thr Ile Cys Ser Arg Ile Gly Ile Thr Asn Tyr Glu Glu
            115                 120                 125

Tyr Ser Leu Ile Gln Glu Thr Ile Glu Glu Lys Lys Glu Glu Gly Thr
            130                 135                 140

Gly Thr Leu Lys Lys Asp Arg Thr Leu Leu Arg Asp Glu Arg Lys Met
145                 150                 155                 160

Glu Lys Leu Lys Ala Lys Leu His Thr Asp Asp Leu Asn Trp Leu
                165                 170                 175

Asp His Ser Arg Thr Phe Arg Glu Gln Gly Val Asp Glu Asn Glu Thr
            180                 185                 190

Leu Leu Leu Arg Arg Lys Phe Phe Tyr Ser Asp Gln Asn Val Asp Ser
            195                 200                 205

Arg Asp Pro Val Gln Leu Asn Leu Leu Tyr Val Gln Ala Arg Asp Asp
            210                 215                 220

Ile Leu Asn Gly Ser His Pro Val Ser Phe Glu Lys Ala Cys Glu Phe
225                 230                 235                 240

Gly Gly Phe Gln Ala Gln Ile Gln Phe Gly Pro His Val Glu His Lys
                245                 250                 255

His Lys Pro Gly Phe Leu Asp Leu Lys Glu Phe Leu Pro Lys Glu Tyr
            260                 265                 270

Ile Lys Gln Arg Gly Ala Glu Lys Arg Ile Phe Gln Glu His Lys Asn
            275                 280                 285

Cys Gly Glu Met Ser Glu Ile Glu Ala Lys Val Lys Tyr Val Lys Leu
            290                 295                 300

Ala Arg Ser Leu Arg Thr Tyr Gly Val Ser Phe Phe Leu Val Lys Glu
305                 310                 315                 320

Lys Met Lys Gly Lys Asn Lys Leu Val Pro Arg Leu Leu Gly Ile Thr
                325                 330                 335

Lys Asp Ser Val Met Arg Val Asp Glu Lys Thr Lys Glu Val Leu Gln
            340                 345                 350

Glu Trp Pro Leu Thr Thr Val Lys Arg Trp Ala Ala Ser Pro Lys Ser
            355                 360                 365

Phe Thr Leu Asp Phe Gly Glu Tyr Gln Glu Ser Tyr Tyr Ser Val Gln
            370                 375                 380

Thr Thr Glu Gly Glu Gln Ile Ser Gln Leu Ile Ala Gly Tyr Ile Asp
385                 390                 395                 400

Ile Ile Leu Lys Lys Lys Gln Ser Lys Asp Arg Phe Gly Leu Glu Gly
                405                 410                 415

Asp Glu Glu Ser Thr Met Leu Glu Glu Ser Val Ser Pro Lys Lys Ser
            420                 425                 430

Thr Ile Leu Gln Gln Gln Phe Asn Arg Thr Gly Lys Ala Glu His Gly
            435                 440                 445

Ser Val Ala Leu Pro Ala Val Met Arg Ser Gly Ser Ser Gly Pro Glu
            450                 455                 460

Thr Phe Asn Val Gly Ser Met Pro Ser Pro Gln Gln Val Met Val
465                 470                 475                 480

Gly Gln Met His Arg Gly His Met Pro Pro Leu Thr Ser Ala Gln Gln
                485                 490                 495

Ala Leu Met Gly Thr Ile Asn Thr Ser Met His Ala Val Gln Gln Ala
            500                 505                 510

Gln Asp Asp Leu Ser Glu Leu Asp Ser Leu Pro Pro Leu Gly Gln Asp
            515                 520                 525
```

-continued

```
Met Ala Ser Arg Val Trp Val Gln Asn Lys Val Asp Glu Ser Lys His
    530                 535                 540

Glu Ile His Ser Gln Val Asp Ala Ile Thr Ala Gly Thr Ala Ser Val
545                 550                 555                 560

Val Asn Leu Thr Ala Gly Asp Pro Ala Asp Thr Asp Tyr Thr Ala Val
                565                 570                 575

Gly Cys Ala Ile Thr Thr Ile Ser Ser Asn Leu Thr Glu Met Ser Lys
                580                 585                 590

Gly Val Lys Leu Leu Ala Ala Leu Met Asp Asp Glu Val Gly Ser Gly
            595                 600                 605

Glu Asp Leu Leu Arg Ala Ala Arg Thr Leu Ala Gly Ala Val Ser Asp
    610                 615                 620

Leu Leu Lys Ala Val Gln Pro Thr Ser Gly Glu Pro Arg Gln Thr Val
625                 630                 635                 640

Leu Thr Ala Ala Gly Ser Ile Gly Gln Ala Ser Gly Asp Leu Leu Arg
                645                 650                 655

Gln Ile Gly Glu Asn Glu Thr Asp Glu Arg Phe Gln Asp Val Leu Met
                660                 665                 670

Ser Leu Ala Lys Ala Val Ala Asn Ala Ala Ala Met Leu Val Leu Lys
            675                 680                 685

Ala Lys Asn Val Ala Gln Val Ala Glu Asp Thr Val Leu Gln Asn Arg
    690                 695                 700

Val Ile Ala Ala Ala Thr Gln Cys Ala Leu Ser Thr Ser Gln Leu Val
705                 710                 715                 720

Ala Cys Ala Lys Val Val Ser Pro Thr Ile Ser Ser Pro Val Cys Gln
                725                 730                 735

Glu Gln Leu Ile Glu Ala Gly Lys Leu Val Asp Arg Ser Val Glu Asn
                740                 745                 750

Cys Val Arg Ala Cys Gln Ala Thr Thr Asp Ser Glu Leu Leu Lys
            755                 760                 765

Gln Val Ser Ala Ala Ala Ser Val Val Ser Gln Ala Leu His Asp Leu
    770                 775                 780

Leu Gln His Val Arg Gln Phe Ala Ser Arg Gly Glu Pro Ile Gly Arg
785                 790                 795                 800

Tyr Asp Gln Ala Thr Asp Thr Ile Met Cys Val Thr Glu Ser Ile Phe
                805                 810                 815

Ser Ser Met Gly Asp Ala Gly Glu Met Val Arg Gln Ala Arg Val Leu
                820                 825                 830

Ala Gln Ala Thr Ser Asp Leu Val Asn Ala Met Arg Ser Asp Ala Glu
            835                 840                 845

Ala Glu Ile Asp Met Glu Asn Ser Lys Lys Leu Leu Ala Ala Ala Lys
    850                 855                 860

Leu Leu Ala Asp Ser Thr Ala Arg Met Val Glu Ala Ala Lys Gly Ala
865                 870                 875                 880

Ala Ala Asn Pro Glu Asn Glu Asp Gln Gln Gln Arg Leu Arg Glu Ala
                885                 890                 895

Ala Glu Gly Leu Arg Val Ala Thr Asn Ala Ala Ala Gln Asn Ala Ile
                900                 905                 910

Lys Lys Lys Ile Val Asn Arg Leu Glu Val Ala Ala Lys Gln Ala Ala
            915                 920                 925

Ala Ala Ala Thr Gln Thr Ile Ala Ala Ser Gln Asn Ala Ala Val Ser
    930                 935                 940
```

-continued

```
Asn Lys Asn Pro Ala Ala Gln Gln Gln Leu Val Gln Ser Cys Lys Ala
945                 950                 955                 960

Val Ala Asp His Ile Pro Gln Leu Val Gln Gly Val Arg Gly Ser Gln
                965                 970                 975

Ala Gln Ala Glu Asp Leu Ser Ala Gln Leu Ala Leu Ile Ile Ser Ser
            980                 985                 990

Gln Asn Phe Leu Gln Pro Gly Ser Lys Met Val Ser Ala Lys Ala
        995                1000                1005

Ala Val Pro Thr Val Ser Asp Gln Ala Ala Met Gln Leu Ser Gln
    1010                1015                1020

Cys Ala Lys Asn Leu Ala Thr Ser Leu Ala Glu Leu Arg Thr Ala Ser
1025                1030                1035                1040

Gln Lys Ala His Glu Ala Cys Gly Pro Met Glu Ile Asp Ser Ala Leu
                1045                1050                1055

Asn Thr Val Gln Thr Leu Lys Asn Glu Leu Gln Asp Ala Lys Met Ala
            1060                1065                1070

Ala Val Glu Ser Gln Leu Lys Pro Leu Pro Gly Glu Thr Leu Glu Lys
        1075                1080                1085

Cys Ala Gln Asp Leu Gly Ser Thr Ser Lys Ala Val Gly Ser Ser Met
    1090                1095                1100

Ala Gln Leu Leu Thr Cys Ala Ala Gln Gly Asn Glu His Tyr Thr Gly
1105                1110                1115                1120

Val Ala Ala Arg Glu Thr Ala Gln Ala Leu Lys Thr Leu Ala Gln Ala
                1125                1130                1135

Ala Arg Gly Val Ala Ala Ser Thr Thr Asp Pro Ala Ala His Ala
            1140                1145                1150

Met Leu Asp Ser Ala Arg Asp Val Met Glu Gly Ser Ala Met Leu Ile
        1155                1160                1165

Gln Glu Ala Lys Gln Ala Leu Ile Ala Pro Gly Asp Ala Glu Arg Gln
    1170                1175                1180

Gln Arg Leu Ala Gln Val Ala Lys Ala Val Ser His Ser Leu Asn Asn
1185                1190                1195                1200

Cys Val Asn Cys Leu Pro Gly Gln Lys Asp Val Asp Val Ala Leu Lys
                1205                1210                1215

Ser Ile Gly Glu Ser Ser Lys Lys Leu Leu Val Asp Ser Leu Pro Pro
            1220                1225                1230

Ser Thr Lys Pro Phe Gln Glu Ala Gln Ser Glu Leu Asn Gln Ala Ala
        1235                1240                1245

Ala Asp Leu Asn Gln Ser Ala Gly Glu Val Val His Ala Thr Arg Gly
    1250                1255                1260

Gln Ser Gly Glu Leu Ala Ala Ala Ser Gly Lys Phe Ser Asp Asp Phe
1265                1270                1275                1280

Asp Glu Phe Leu Asp Ala Gly Ile Glu Met Ala Gly Gln Ala Gln Thr
                1285                1290                1295

Lys Glu Asp Gln Ile Gln Val Ile Gly Asn Leu Lys Asn Ile Ser Met
            1300                1305                1310

Ala Ser Ser Lys Leu Leu Leu Ala Ala Lys Ser Leu Ser Val Asp Pro
        1315                1320                1325

Gly Ala Pro Asn Ala Lys Asn Leu Leu Ala Ala Ala Arg Ala Val
    1330                1335                1340

Thr Glu Ser Ile Asn Gln Leu Ile Thr Leu Cys Thr Gln Gln Ala Pro
1345                1350                1355                1360

Gly Gln Lys Glu Cys Asp Asn Ala Leu Arg Glu Leu Glu Thr Val Lys
```

-continued

```
                1365                1370                1375
Gly Met Leu Asp Asn Pro Asn Glu Pro Val Ser Asp Leu Ser Tyr Phe
                1380                1385                1390
Asp Cys Ile Glu Ser Val Met Glu Asn Ser Lys Val Leu Gly Glu Ser
                1395                1400                1405
Met Ala Gly Ile Ser Gln Asn Ala Lys Thr Gly Asp Leu Pro Ala Phe
                1410                1415                1420
Gly Glu Cys Val Gly Ile Ala Ser Lys Ala Leu Cys Gly Leu Thr Glu
1425                1430                1435                1440
Ala Ala Ala Gln Ala Ala Tyr Leu Val Gly Ile Ser Asp Pro Asn Ser
                1445                1450                1455
Gln Ala Gly His Gln Gly Leu Val Asp Pro Ile Gln Phe Ala Arg Ala
                1460                1465                1470
Asn Gln Ala Ile Gln Met Ala Cys Gln Asn Leu Val Asp Pro Gly Ser
                1475                1480                1485
Ser Pro Ser Gln Val Leu Ser Ala Ala Thr Ile Val Ala Lys His Thr
                1490                1495                1500
Ser Ala Leu Cys Asn Ala Cys Arg Ile Ala Ser Ser Lys Thr Ala Asn
1505                1510                1515                1520
Pro Val Ala Lys Arg His Phe Val Gln Ser Ala Lys Glu Val Ala Asn
                1525                1530                1535
Ser Thr Ala Asn Leu Val Lys Thr Ile Lys Ala Leu Asp Gly Asp Phe
                1540                1545                1550
Ser Glu Asp Asn Arg Asn Lys Cys Arg Ile Ala Thr Ala Pro Leu Ile
                1555                1560                1565
Glu Ala Val Glu Asn Leu Thr Ala Phe Ala Ser Asn Pro Glu Phe Val
                1570                1575                1580
Ser Ile Pro Ala Gln Ile Ser Ser Glu Gly Ser Gln Ala Gln Glu Pro
1585                1590                1595                1600
Ile Leu Val Ser Ala Lys Thr Met Leu Glu Ser Ser Ser Tyr Leu Ile
                1605                1610                1615
Arg Thr Ala Arg Ser Leu Ala Ile Asn Pro Lys Asp Pro Pro Thr Trp
                1620                1625                1630
Ser Val Leu Ala Gly His Ser His Thr Val Ser Asp Ser Ile Lys Ser
                1635                1640                1645
Leu Ile Thr Ser Ile Arg Asp Lys Ala Pro Gly Gln Arg Glu Cys Asp
                1650                1655                1660
Tyr Ser Ile Asp Gly Ile Asn Arg Cys Ile Arg Asp Ile Glu Gln Ala
1665                1670                1675                1680
Ser Leu Ala Ala Val Ser Gln Ser Leu Ala Thr Arg Asp Asp Ile Ser
                1685                1690                1695
Val Glu Ala Leu Gln Glu Gln Leu Thr Ser Val Val Gln Glu Ile Gly
                1700                1705                1710
His Leu Ile Asp Pro Ile Ala Thr Ala Ala Arg Gly Glu Ala Ala Gln
                1715                1720                1725
Leu Gly His Lys Val Thr Gln Leu Ala Ser Tyr Phe Glu Pro Leu Ile
                1730                1735                1740
Leu Ala Ala Val Gly Val Ala Ser Lys Ile Leu Asp His Gln Gln Gln
                1745                1750                1755                1760
Met Thr Val Leu Asp Gln Thr Lys Thr Leu Ala Glu Ser Ala Leu Gln
                1765                1770                1775
Met Leu Tyr Ala Ala Lys Glu Gly Gly Gly Asn Pro Lys Ala Gln His
                1780                1785                1790
```

```
Thr His Asp Ala Ile Thr Glu Ala Ala Gln Leu Met Lys Glu Ala Val
        1795                1800                1805

Asp Asp Ile Met Val Thr Leu Asn Glu Ala Ala Ser Glu Val Gly Leu
    1810                1815                1820

Val Gly Gly Met Val Asp Ala Ile Ala Glu Ala Met Ser Lys Leu Asp
1825                1830                1835                1840

Glu Gly Thr Pro Pro Glu Pro Lys Gly Thr Phe Val Asp Tyr Gln Thr
                1845                1850                1855

Thr Val Val Lys Tyr Ser Lys Ala Ile Ala Val Thr Ala Gln Glu Met
            1860                1865                1870

Met Thr Lys Ser Val Thr Asn Pro Glu Glu Leu Gly Gly Leu Ala Ser
        1875                1880                1885

Gln Met Thr Ser Asp Tyr Gly His Leu Ala Phe Gln Gly Gln Met Ala
    1890                1895                1900

Ala Ala Thr Ala Glu Pro Glu Glu Ile Gly Phe Gln Ile Arg Thr Arg
1905                1910                1915                1920

Val Gln Asp Leu Gly His Gly Cys Ile Phe Leu Val Gln Lys Ala Gly
                1925                1930                1935

Ala Leu Gln Val Cys Pro Thr Asp Ser Tyr Thr Lys Arg Glu Leu Ile
            1940                1945                1950

Glu Cys Ala Arg Ala Val Thr Glu Lys Val Ser Leu Val Leu Ser Ala
        1955                1960                1965

Leu Gln Ala Gly Asn Lys Gly Thr Gln Ala Cys Ile Thr Ala Ala Thr
    1970                1975                1980

Ala Val Ser Gly Ile Ile Ala Asp Leu Asp Thr Thr Ile Met Phe Ala
1985                1990                1995                2000

Thr Ala Gly Thr Leu Asn Ala Glu Asn Ser Glu Thr Phe Ala Asp His
                2005                2010                2015

Arg Glu Asn Ile Leu Lys Thr Ala Lys Ala Leu Val Glu Asp Thr Lys
            2020                2025                2030

Leu Leu Val Ser Gly Ala Ala Ser Thr Pro Asp Lys Leu Ala Gln Ala
        2035                2040                2045

Ala Gln Ser Ser Ala Ala Thr Ile Thr Gln Leu Ala Glu Val Val Lys
    2050                2055                2060

Leu Gly Ala Ala Ser Leu Gly Ser Asp Asp Pro Glu Thr Gln Val Val
2065                2070                2075                2080

Leu Ile Asn Ala Ile Lys Asp Val Ala Lys Ala Leu Ser Asp Leu Ile
                2085                2090                2095

Ser Ala Thr Lys Gly Ala Ala Ser Lys Pro Val Asp Asp Pro Ser Met
            2100                2105                2110

Tyr Gln Leu Lys Gly Ala Ala Lys Val Met Val Thr Asn Val Thr Ser
        2115                2120                2125

Leu Leu Lys Thr Val Lys Ala Val Glu Asp Glu Ala Thr Arg Gly Thr
    2130                2135                2140

Arg Ala Leu Glu Ala Thr Ile Glu Cys Ile Lys Gln Glu Leu Thr Val
2145                2150                2155                2160

Phe Gln Ser Lys Asp Val Pro Glu Lys Thr Ser Ser Pro Glu Glu Ser
                2165                2170                2175

Ile Arg Met Thr Lys Gly Ile Thr Met Ala Thr Ala Lys Ala Val Ala
            2180                2185                2190

Ala Gly Asn Ser Cys Arg Gln Glu Asp Val Ile Ala Thr Ala Asn Leu
        2195                2200                2205
```

```
                                      -continued
Ser Arg Lys Ala Val Ser Asp Met Leu Thr Ala Cys Lys Gln Ala Ser
    2210            2215            2220

Phe His Pro Asp Val Ser Asp Glu Val Arg Thr Arg Ala Leu Arg Phe
2225            2230            2235            2240

Gly Thr Glu Cys Thr Leu Gly Tyr Leu Asp Leu Leu Glu His Val Leu
                2245            2250            2255

Val Ile Leu Gln Lys Pro Thr Pro Glu Phe Lys Gln Gln Leu Ala Ala
            2260            2265            2270

Phe Ser Lys Arg Val Ala Gly Ala Val Thr Glu Leu Ile Gln Ala Ala
            2275            2280            2285

Glu Ala Met Lys Gly Thr Glu Trp Val Asp Pro Glu Asp Pro Thr Val
    2290            2295            2300

Ile Ala Glu Thr Glu Leu Leu Gly Ala Ala Ala Ser Ile Glu Ala Ala
2305            2310            2315            2320

Ala Lys Lys Leu Glu Gln Leu Lys Pro Arg Ala Lys Pro Lys Gln Ala
                2325            2330            2335

Asp Glu Thr Leu Asp Phe Glu Gln Gln Ile Leu Glu Ala Ala Lys Ser
            2340            2345            2350

Ile Ala Ala Ala Thr Ser Ala Leu Val Lys Ser Ala Ser Ala Ala Gln
            2355            2360            2365

Arg Glu Leu Val Ala Gln Gly Lys Val Gly Ser Ile Pro Ala Asn Ala
    2370            2375            2380

Ala Asp Asp Gly Gln Trp Ser Gln Gly Leu Ile Ser Ala Ala Arg Met
2385            2390            2395            2400

Val Ala Ala Ala Thr Ser Ser Leu Cys Glu Ala Ala Asn Ala Ser Val
                2405            2410            2415

Gln Gly His Ala Ser Glu Glu Lys Leu Ile Ser Ser Ala Lys Gln Val
                2420            2425            2430

Ala Ala Ser Thr Ala Gln Leu Leu Val Ala Cys Lys Val Lys Ala Asp
            2435            2440            2445

Gln Asp Ser Glu Ala Met Arg Arg Leu Gln Ala Ala Gly Asn Ala Val
    2450            2455            2460

Lys Arg Ala Ser Asp Asn Leu Val Arg Ala Ala Gln Lys Ala Ala Phe
2465            2470            2475            2480

Gly Lys Ala Asp Asp Asp Asp Val Val Val Lys Thr Lys Phe Val Gly
            2485            2490            2495

Gly Ile Ala Gln Ile Ile Ala Ala Gln Glu Glu Met Leu Lys Lys Glu
            2500            2505            2510

Arg Glu Leu Glu Glu Ala Arg Lys Lys Leu Ala Gln Ile Arg Gln Gln
            2515            2520            2525

Gln Tyr Lys Phe Leu Pro Thr Glu Leu Arg Glu Asp Glu Gly
    2530            2535            2540
```